United States Patent [19]

Shannon

[11] 4,097,345
[45] Jun. 27, 1978

[54] $NA_5GDSI_4O_{12}$ AND RELATED RARE EARTH SODIUM ION CONDUCTORS AND ELECTROLYTIC CELLS THEREFROM

[75] Inventor: Robert Day Shannon, Wilmington, Del.

[73] Assignee: E. I. Du Pont de Nemours and Company, Wilmington, Del.

[21] Appl. No.: 732,748

[22] Filed: Oct. 15, 1976

[51] Int. Cl.² .................. C25D 5/00; C25D 17/00; H01M 4/36; H01B 1/00
[52] U.S. Cl. .................. 204/59 AM; 204/195 S; 204/242; 252/520; 252/521; 429/104; 429/191; 429/193
[58] Field of Search .................. 429/104, 191, 193; 204/195 S, 242; 252/520, 521

[56] References Cited

U.S. PATENT DOCUMENTS

| 3,829,331 | 8/1974 | Tsang | 429/104 |
|---|---|---|---|
| 4,042,482 | 8/1977 | Shannon et al. | 204/242 |
| 4,049,891 | 9/1977 | Hong et al. | 429/193 |

FOREIGN PATENT DOCUMENTS

| 48,685 | 12/1972 | Japan | 429/193 |
|---|---|---|---|
| 12,566 | 5/1975 | Japan | 429/191 |

OTHER PUBLICATIONS

Maksimov et al., Soviet Physics–Crystallography, vol. 14, No. 3, pp. 407–410, 12/69.
Maksimov et al., Soviet Physics Dokl–Crystallography, vol. 15, No. 12, p. 76, 6/74.

*Primary Examiner*—F.C. Edmundson

[57] ABSTRACT

Sodium ion conducting compositions are provided having (a) the formula $Na_{5-x}\square_xGd_{1-y-x}M_yM'_xSi_{4-z}Ge_zO_{12}$ wherein
 M is at least one of the rare earths or yttrium,
 M' is $Zr^{4+}$, $Hf^{4+}$, or $Th^{4+}$,
 $\square$ is a sodium vacancy to preserve charge neutrality,
 x is 0 to about 0.5 when $Zr^{4+}$ or $Hf^{4+}$ is included in M' and 0 to about 0.1 when $Th^{4+}$ is included in M',
 y is 0 to 1, and
 z is 0 to 4, with the proviso that y + x is no more than 1, and (b) the rhombohedral $Na_5YSi_4O_{12}$ crystal structure with space group symmetry $R\bar{3}c$. These compositions are useful as solid electrolytes in electrochemical cells such as galvanic cells and electrolytic cells.

Certain of the sodium ion conducting compositions are novel compositions of matter.

42 Claims, 7 Drawing Figures

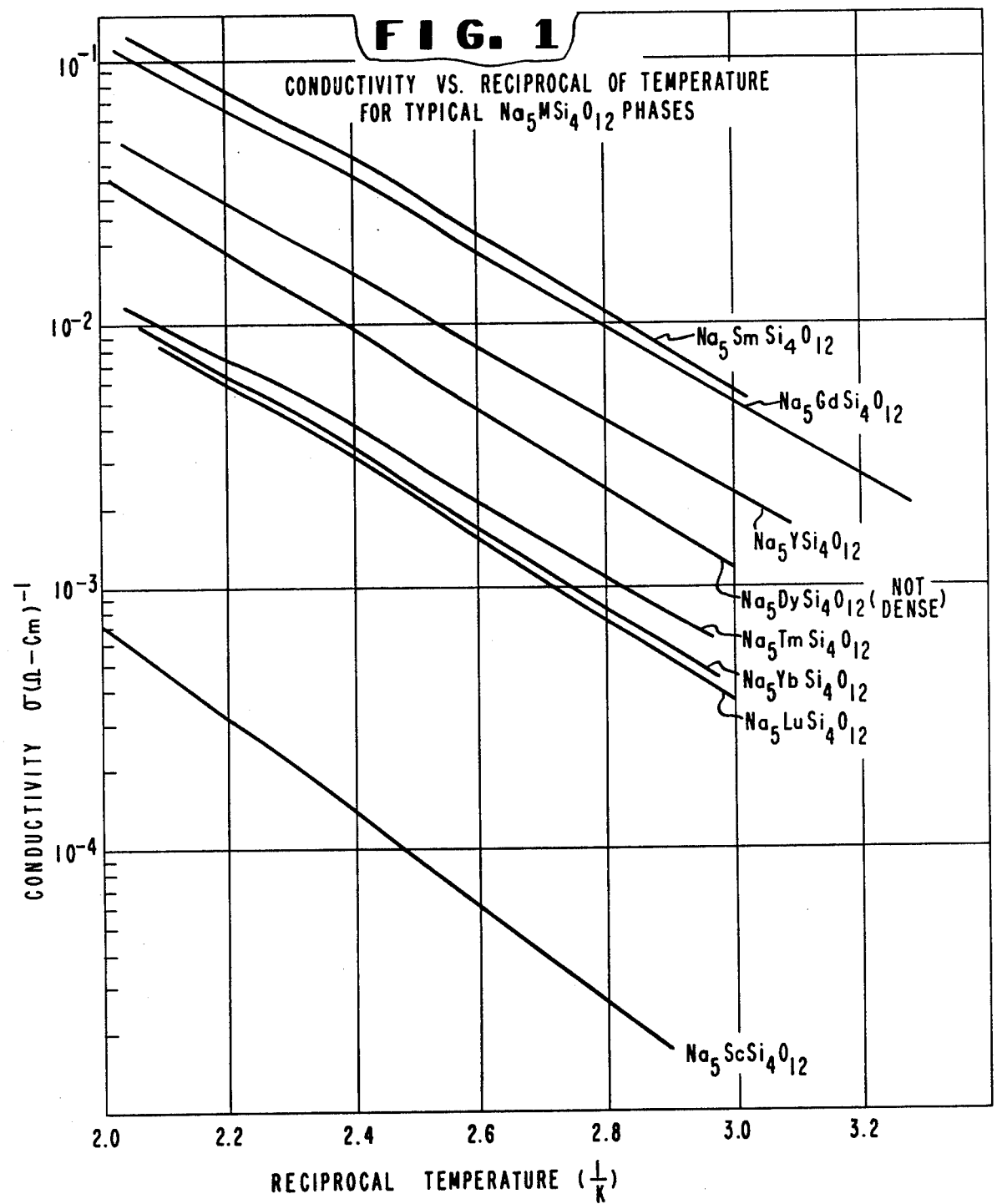
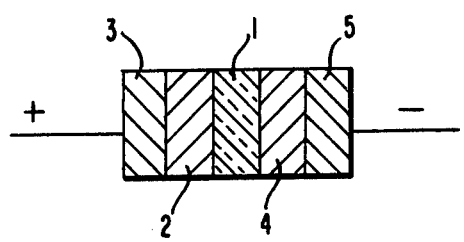

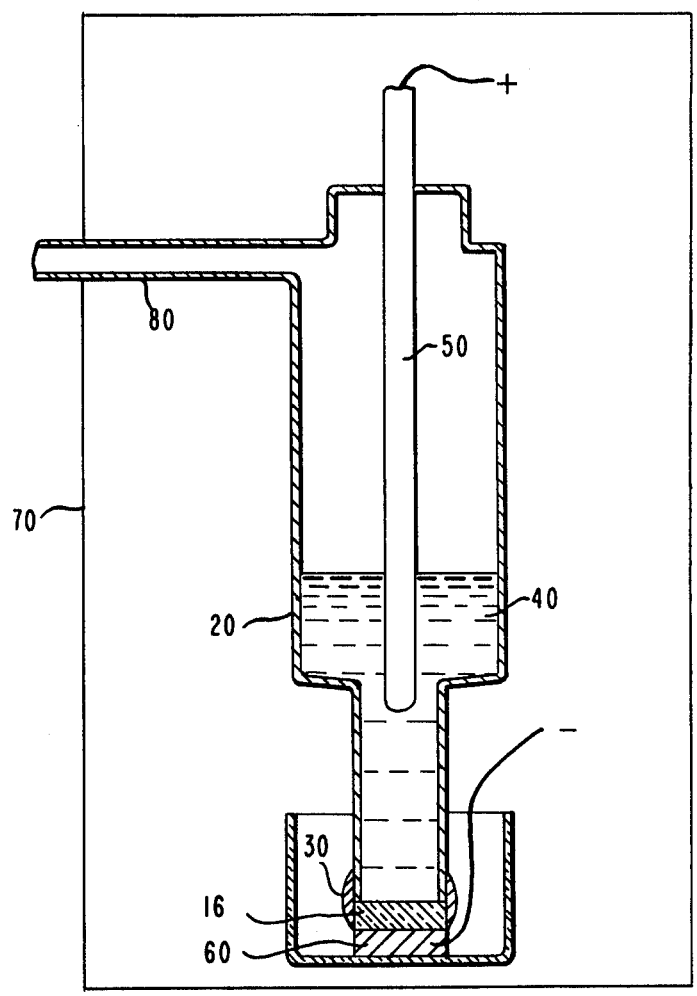

$Na_5GdSi_4O_{12}$ AND RELATED RARE EARTH SODIUM ION CONDUCTORS AND ELECTROLYTIC CELLS THEREFROM

BACKGROUND OF THE INVENTION

1. Field of the Invention

This invention relates to $Na^+$-conducting sodium rare earth silicates and their use as solid electrolytes in electrochemical cells such as batteries and electrolytic cells, such as sodium electrowinning cells.

2. Description of the Prior Art

Solid ionic conductors with $Na^+$ as the mobile species are desirable for use as solid electrolytes.

Na has long been regarded as a desirable component of galvanic cells. It is inexpensive and its high reduction potential and light weight have often suggested its use as the anodic component in high energy-density storage batteries. $Na^+$ conductors such as $\beta$-$Al_2O_3$ which are solid and are highly conductive at low temperatures are quite useful in such utilities; these conductors also serve to separate the anodic and cathodic components. (See, for example, J. T. Kummer, Prog. in Solid State Chem., 7, 141 (1972), J. T. Kummer and N. Weber, "A Sodium-Sulfur Secondary Battery" SAE paper No. 670179, Jan. 1967, and L. S. Marcoux and E. T. Seo, "Sodium-Sulfur Batteries" in Amer. Chem. Soc. Monongraph on New Uses of Sulfur, 1975.)

Solid electrolytes and in particular completely solid state galvanic cells offer special advantages as primary batteries. These advantages include the possibility for long shelf life, broad temperature limits of operability and minaturization. A $Na^+$ conducting solid electrolyte would provide a lighter and lower cost alternative to the solid state batteries which rely on the transport of $Ag^+$ in various silver halides.

The best $Na^+$ ionic conductors known at present are $\beta$- and $\beta''$-$Al_2O_3$ whose compositions are approximately Na $Al_{11}O_{17}$. Conductivities at 300° C are of the order of $10^{-1} (\Omega\text{-cm})^{-1}$ and at room temperature of the order of $10^{-2} (\Omega\text{-cm})^{-1}$. Conductivity data for $\beta$-$Al_2O_3$ solid electrolytes is given by M. S. Whittingham and R. A. Huggins, Proc. of the 5th Materials Research Symposium (National Bureau of Stds. Special Publication 364, pp. 139-154) and by J. T. Kummer, Prog. in Solid State Chem. 7, 141 (1972).

Conductivities comparable to those obtained for $\beta$- and $\beta''$-$Al_2O_3$ have recently been reported by Goodenough et al (Mat. Res. Bull. 11, 203 (1976) for $Na_3Zr_2PSi_2O_{12}$ and related compositions. A conductivity of 0.2 (ohm cm)$^{-1}$ is reported at 300° C.

The compounds $Na_5FeSi_4O_{12}$, $Na_5ScSi_4O_{12}$, $Na_5ErSi_4O_{12}$ and $Na_5YSi_4O_{12}$ have previously been prepared. Bowen, Schairer and Willems in 1930 (Amer. J. Sci., 20, 405 (1930)) found $Na_5FeSi_4O_{12}$ in their investigation of the $Na_2O$-$Fe_2O_3$-$SiO_2$ phase diagram. The compound $Na_5FeSi_4O_{12}$ was prepared by making a glass from $Na_2SiO_3$, $SiO_2$, and $Fe_2O_3$ at elevated temperatures and subsequently annealing the glass. Crystals were isolated from the melt and the optical properties and crystal system but not the unit cell or crystal structure, were determined. Maksimov et al Sov. Phys.-Cryst. 14, 407 (1969) reported the hydrothermal synthesis (450° C, 1500 atm) of monoclinic $Na_5YSi_4O_{12}$. The crystal structure of $Na_5YSi_4O_{12}$ was reported by Maksimov et al Sov. Phys.-Dokl. 18, 763 (1974) as monoclinic (space group = $B2/b$) but pseudo rhombohedral (space group = $\bar{R}3c$). The isostructural compounds $Na_5ScSi_4O_{12}$, $Na_5ErSi_4O_{12}$, and $Na_5FeSi_4O_{12}$ are also mentioned and it is stated that these compounds can be made by hydrothermal synthesis and only if Fe is present in the charge.

Similar structural features and synthetic conditions were given for various Na-Sc and Na-Y silicates and germanates by Maksimov et al at the 10th International Congress of Crystallography, August 1975.

No mention of ionic conductivity was made in any of these previous works on $Na_5MSi_4O_{12}$ compounds.

SUMMARY OF THE INVENTION

According to the present invention there is provided a sodium ion conducting composition having (a) the formula $Na_{5-x}\square_x Gd_{1-y-x}M_y M'_x Si_{4-z}Ge_z O_{12}$ wherein M is at least one of the rare earths or yttrium,
M' is $Zr^{4+}$, $Hf^{4+}$, or $Th^{4+}$,
$\square$ is a sodium vacancy to preserve charge neutrality,
x is 0 to about 0.5 when $Zr^{4+}$ or $Hf^{4+}$ is included in M' and 0 to about 0.1 when $Th^{4+}$ is included in M',
y is 0 to 1, and
z is 0 to 4, with the proviso that $y+x$ is no more than 1, and (b) the rhombohedral $Na_5YSi_4O_{12}$ crystal structure with space group symmetry $\bar{R}3c$.

There is also provided an electrochemical device for transporting sodium ions having (a) two electrodes one of which is sodium, (b) a solid electrolyte separating the two electrodes, and (c) an inert connecting electrical connector to complete an electrical circuit between the two electrodes wherein the solid electrolyte consists essentially of the aforesaid composition.

Also provided in a novel sodium rare earth silicate and/or germanate having the formula

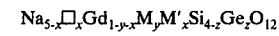

wherein

M is at least one of $Ho^{3+}$, $Sm^{3+}$, $Tb^{3+}$, $Dy^{3+}$, $Nd^{3+}$, $Pr^{3+}$ and $La^{3+}$,
M' is $Zr^{4+}$, $Hf^{4+}$ or $Th^{4+}$,
$\square$ is a sodium vacancy to preserve charge neutrality,
z is 0 to 4,
x is 0 to about 0.5 when $Zr^{4+}$ or $Hf^{4+}$ is included in M' and 0 to about 0.1 when $Th^{4+}$ is included in M',
y is (1) 0 to 1 when M is $Ho^{3+}$, $Sm^{3+}$, $Tb^{3+}$ or $Dy^{3+}$,
(2) 0 to about 0.6 when M is $Nd^{3+}$,
(3) 0 to about 0.4 when M is $Pr^{3+}$, and
(4) 0 to about 0.2 when M is $La^{3+}$ with the proviso that $y+x$ can be no more than 1.

BRIEF DESCRIPTION OF THE DRAWINGS

FIG. 1 is a graph of the temperature dependence of $Na^+$ conductivity of various $Na_5MSi_4O_{12}$ compositions;

FIG. 2 is an illustrative, cross-sectional view of a primary cell using a sodium rare earth silicate solid electrolyte;

FIG. 3 is an illustrative, cross-sectional view of a sodium electrowinning cell using a sodium rare earth silicate solid electrolyte;

DETAILED DESCRIPTION OF THE INVENTION

Figure 4:
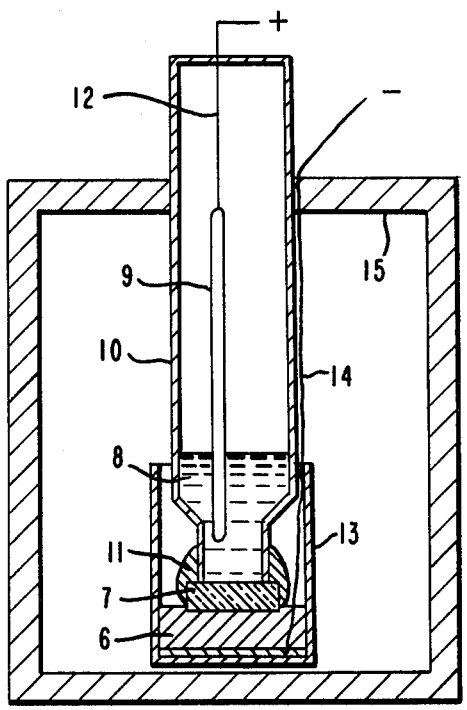
FIG. 4 is an illustrative, cross-sectional view of a sodium-sulfur voltaic cell.

The sodium rare earth silicates and germanates of this invention are crystalline solids which exhibit good $Na^+$ conduction. For example, at 200° C conductivities of the order of $10^{-1} (\Omega\ cm)^{-1}$ have been observed. Conductivities of this order of magnitude allow these materials to be useful as solid electrolytes in batteries, coulometers, timers, display devices, and in sodium-winning and sodium-purifying cells. (See M. Voinov, "Various Utilizations of Solid Electrolytes" In Electronic Processes in Solid State Ionics, Proc. Nato Adv. Study Institute held in Ajaccio, Corsica, Aug. 23 - Sept. 9, 1975, ed. M. Kleitz and J. DuPuy, D. Reidel Publ. Co. Boston, 1976).

The compositions in which this ionic conductivity has been found have the $Na_5YSi_4O_{12}$ rhombohedral crystal structure with space group $R\bar{3}c$ and the general formula:

$$Na_{5-x}\square_x Gd_{1-y-x}M_y M'_x Si_{4-z}Ge_z O_{12}$$

wherein

M is at least one of the rare earths or yttrium,
M′ is $Zr^{4+}$, $Hf^{4+}$, or $Th^{4+}$,
$\square$ is a sodium vacancy to preserve charge neutrality,
x is 0 to about 0.5 when $Zr^{4+}$ or $Hf^{4+}$ is included in M′ and 0 to about 0.1 when $Th^{4+}$ is included in M′,
y is 0 to 1, and
z is 0 to 4, with the proviso that $y+x$ is no more than 1.

Preferred sodium ion conducting compositions are the silicates, i.e., where z is 0 in the aforesaid formula. Preferred rare earths M are at least one of $Ho^{3+}$, $Sm^{3+}$, $Tb^{3+}$, $Dy^{3+}$, $Nd^{3+}$, $Pr^{3+}$, and $La^{3+}$ and y is
(1) 0 to 1 when M is $Ho^{3+}$, $Sm^{3+}$, $Tb^{3+}$ or $Dy^{3+}$,
(2) 0 to about 0.6 when M is $Nd^{3+}$,
(3) 0 to about 0.4 when M is $Pr^{3+}$, and
(4) 0 to about 0.2 when M is $La^{3+}$.
M′ in the preferred compositions is preferably $Zr^{4+}$.

Examples of especially preferred sodium ion conducting compositions are $Na_5GdSi_4O_{12}$, $Na_5SmSi_4O_{12}$, $Na_5HoSi_4O_{12}$, $Na_5TbSi_4O_{12}$, $Na_{4.9-4.8}Gd_{9-.8}Zr_{.1-.2}Si_4O_{12}$, $Na_5Gd_{.8-.4}Nd_{.2-.6}Si_4O_{12}$, $Na_5Gd_{.8}La_{.2}Si_4O_{12}$, $Na_{4.9}Gd_{.7}Nd_{.2}Zr_{.1}Si_4O_{12}$, $Na_5Gd_{.8-.6}Pr_{.2-.4}Si_4O_{12}$.

Many of the sodium ion conducting compositions are novel compositions of matter. These compositions have the formula:

$$Na_{5-x}\square_x Gd_{1-y-x}M_y M'_x Si_{4-z}Ge_z O_{12}$$

wherein

M is at least one of $Ho^{3+}$, $Sm^{3+}$, $Tb^{3+}$, $Dy^{3+}$, $Nd^{3+}$, $Pr^{3+}$ and $La^{3+}$,
M′ is $Zr^{4+}$, $Hf^{4+}$ or $Th^{4+}$,
$\square$ is a sodium vacancy to preserve charge neutrality,
z is 0 to 4,
x is 0 to about 0.5 when $Zr^{4+}$ or $Hf^{4+}$ is included in M′ and 0 to about 0.1 when $Th^{4+}$ is included in M′,
y is (1) 0 to 1 when M is $Ho^{3+}$, $Sm^{3+}$, $Tb^{3+}$ or $Dy^{3+}$,
(2) 0 to about 0.6 when M is $Nd^{3+}$,
(3) 0 to about 0.4 when M is $Pr^{3+}$, and
(4) 0 to about 0.2 when M is $La^{3+}$ with the proviso that $y+x$ can be no more than 1.

Here again, the preferred compositions are the silicates (z = 0) and M′ is preferably $Zr^{4+}$.

The compositions of this invention can be prepared by conventional solid state reaction methods. The reactants, which are preferably reagent or commercial grade oxides, hydroxides, carbonates, nitrates, silicates or the like, are thoroughly mixed in amounts dictated by the desired stoichiometry. Mixing can be done dry by conventional ball milling or grinding in a mortar. Mixing can also be accomplished by mixing aqueous solutions containing the proper ratios of sodium, rare earths, other metals (if desired) and silicon. The starting solutions are typically prepared using rare earth nitrates and sodium silicate. The water is evaporated, the precipitate mixture dried and then calcined at 700° C for 16 hours.

The mixture of reactants is heated in a crucible made of any material which will not react with the product, e.g., platinum, silver or gold can be used. The temperature of the reaction must be sufficient so as to allow the components to react. As is the case for many solid state reactions, processing temperatures approximately 100°–200° C below the melting temperature of any given composition are generally satisfactory. For the preferred compositions this corresponds to reaction temperatures of about 800°–1050° C. The reaction temperature for yttrium-containing compositions will be slightly higher.

The reaction time is not critical but should be sufficient to allow essentially complete reaction of the components. Usually 8–24 hr is satisfactory. As is well known to those familiar with solid state reactions, in order to promote the completion of the reaction it is frequently advantageous to interrupt the heating and regrind the product. Frequently after one grinding and heating cycle an intermediate phase appears. This phase may have a composition close to $Na_5MSi_4O_{12}$ or may be of the type $Na_3MSi_3O_9$ which would then be accompanied by amorphous $Na_2SiO_3$. Since the $Na_3MSi_3O_9$ compounds are not especially conductive, the conductivity of samples containing these phases is lower than pure $Na_5MSi_4O_{12}$ samples. Consequently, the process of successive grinding and heating should be repeated until there are no impurity phases present as evidenced by the absence of foreign diffraction peaks on an X-ray diffraction pattern. Upon completion of the heating cycle, the sample can either be air or water quenched, or cooled in the furnace.

In contrast to the syntheses previously reported for compounds of this structure, normal air sintering techniques can be used to prepare any of the compounds of the type $Na_5MSi_4O_{12}$. Hydrothermal synthesis is not necessary and $Fe^{3+}$ does not have to be present. In addition, $Na_5GdSi_4O_{12}$ cannot be prepared using the hydrothermal conditions favorable for the formation of $Na_5YSi_4O_{12}$, despite a wide variety of concentrations of NaOH and $Gd_2O_3$ - $SiO_2$ ratios.

A characteristic feature of the compounds of this invention is their rhombohedral crystal structure with space group symmetry $R\bar{3}c$ as typified by $Na_5YSi_4O_{12}$. The structure of $Na_5YSi_4O_{12}$ is characterized by $SiO_4$ tetrahedra linked in such a way as to form $Si_{12}O_{36}$ rings which are, in turn, linked to each other by $YO_6$ octahedra. The combination of these octahedra and $Si_{12}O_{36}$ rings provides a framework structure with three-dimensionally linked channels through which, it is believed, some or all of the $Na^+$ ions may move. The term "framework structure" implies that the $Y_3Si_{12}O_{36}$ group provides structural integrity and the movement of $Na^+$ ions with breaking of Na - O bonds does not result in collapse of the structure. The dimensions of the unit cells and the cell volumes of the $Na_5MSi_4O_{12}$ phases are directly related to the average radii of the M ions. The larger the size of the M ions, the larger the channels through which the $Na^+$ ions move and the higher the ionic conductivity. The size of M ions cannot be increased without limit however, since the stability of the ionically conducting $Na_5YSi_4O_{12}$-type structure is maintained only up to a maximum volume of the unit cell or alternatively by the maximum average ionic radius $r$ of the M ions. For $Na_5MSi_4O_{12}$ phases, this limit on the cell volume is about 5400 $A^3$ and the limit on the average M radius $\bar{r}$ is approximately 0.96 A. For $Na_5MGe_4O_{12}$ phases the limit on the cell volume is about 5840 $A^3$.

The extent of substitution of the larger rare earth ions $Nd^{3+}$, $Pr^{3+}$, and $La^{3+}$ is determined by the stability of the $Na_5YSi_4O_{12}$ structure and must be done in conjunction with a smaller rare earth ion in order to keep $\bar{r}$ below the limiting value. Values close to the limiting value can be achieved for example by $Gd_{.8}La_{.2}(\bar{r} = 0.956A)$, $Gd_{.6}Pr_{.4}(\bar{r} = 0.958A)$, $Gd_{.4}Nd_{.6}(\bar{r} = 0.965A)$, or $Sm(\bar{r} = 0.958A)$. Substituting the larger rare earths Nd, Pr, and La for Gd is particularly desirable because of the lower cost of the larger ion materials.

The rhombohedral crystal structure can be determined from the characteristic X-ray diffraction pattern that is readily obtained by a number of methods as described in standard references such as B. D. Cullity "Elements of X-ray Diffraction" Addison-Wesley, Reading, Mass. (1956). The Hägg-Guinier powder diffraction patterns of all the compositions of this invention are quite similar and closely resemble that of $Na_5YSi_4O_{12}$.

The conductivities of the products of this invention can be measured by both a-c and d-c methods using Na electrodes. The powder products of this invention are prepared in the form of discs with thicknesses between 0.45 cm and 1.2 cm and diameters between 1.1 cm and 1.25 cm chosen for convenience. These discs are generally prepared by sintering, i.e., the powder pressed in a steel die at a pressure of the order of 30,000 psi and the discs then heated to a temperature of about 1000° C for 4 hr and rapidly cooled in air. Alternatively, the pressed discs can be hotpressed by placing them in a graphite die. The pressure, temperature and time of pressure is not critical but a typical sample is pressed at a pressure of 4000 psi while heating at a temperature of 1000° C for 15 minutes. A disc to be measured for conductivity is mounted in a stainless steel holder between two discs of Na foil, 0.015 inch thick, supported on Ni screens. The sample temperature is raised above the melting point of Na metal to assure good contact. The a-c conductance is measured using a Wayne-Kerr universal bridge at a frequency of $10^4$ rad/sec. The dc conductivity is checked by applying slowly varying voltages (triangular wave forms with a frequency less than 0.01 Hz) and recording the current. Conductivity is calculated from the current-voltage plots. Excellent agreement with the ac results are obtained.

Plots of the conductivity of typical $Na_5MSi_4O_{12}$ compositions are shown in FIG. 1. It is apparent that the level of conductivity increases as the size of the $M^{3+}$ ion increases (See R. D. Shannon and C. T. Prewitt, Acta Cryst. B25, 925 (1969) for a compilation of ionic sizes of rare earth ions) or alternatively as the atomic number of the rare earth decreases. The discs used for conductivity measurements shown in FIG. 1 were prepared by sintering as shown in the examples. The density of these discs varied from about 70% to 95% of theoretical density. Because the level of conductivity depends somewhat on the density of the sample, the values shown in FIG. 1 can vary by a factor of 2 or 3 from one sample to another. Ideal conductivity values can be obtained from 100% theoretical density with samples less dense than 100% of theoretical resulting in lower conductivities.

Because the highest levels of conductivity are associated with the largest M ions, it is to be understood that the most desirable compositions are those containing the largest rare earths consistent with the $Na_5YSi_4O_{12}$ structure with the proviso that the particular rare earth in question have a stable oxidation state, i.e., it should not be reduced by Na metal. Thus, although the radius of $Sm^{3+}$ is larger than that of $Gd^{3+}$, its tendency to be reduced to $Sm^{2+}$ in the presence of liquid Na makes it less desirable for applications involving liquid Na. Similar considerations are valid for the substitution of Ge for Si.

Ionic conductivity is highest in those compositions $Na_5MSi_4O_{12}$ in which M is composed only of one or more rare earths. Those substitutions for M which do not significantly change the unit cell volume (or alternatively the average radius of the M ion, $\bar{r}$) do not significantly alter the conductivity. However, compositions which significantly reduce the cell volume such as Fe, Sc or Lu decrease the conductivity according to the degree of cell volume reduction, e.g., see FIG. 1. Substitutions for some of the Na generally result in decreases in ionic conductivity. Substitution of small quantities of some materials can provide other benefits without seriously affecting the conductivity. For example, the combination of $Zr^{4+}$ and Na vacancies at about $x \cong 0.05$–0.10 improves the sinterability of the product and allows preparation of dense ceramics without resulting in any appreciable decrease in $Na^+$ conductivity from that obtained with the unsubstituted composition.

The presence of non-conductive impurity phases reduces the ionic conductivity. However, so long as the major phase present is the conductive $Na_5MSi_4O_{12}$ phase, the sample still shows good conductivity.

Small quantities of $Na_2SO_4$ or $Na_3PO_4$ (1–2 mole %) can be added to improve the reaction kinetics to give a dense polycrystalline product. The mechanism is not understood but it may be that some $S^{6+}$ or $P^{5+}$ enters the silicate framework with the simultaneous introduction of Na vacancies and consequent increase of sintering rate. This behavior may be similar to the introduction of $Zr^{4+}$ and Na vacancies. It is also possible that the $Na_2SO_4$ or $Na_3PO_4$ forms a liquid phase at or near the grain boundaries. The presence of liquid phases in polycrystalline ceramics is known to frequently allow the rapid attainment of a dense pore-free material.

New two-phase compositions have been discovered which yield highly conducting ceramic samples. Attempts to substitute Ba for Na in $Na_5YSi_4O_{12}$ or $Na_5GdSi_4O_{12}$ phases have resulted in two-phase products that sinter well to give dense ceramic shapes. The primary phase (80–100 mole percent) is the conductive $Na_5MSi_4O_{12}$ phase but an additional impurity phase (up to 20 mole percent), which appears to be $Na_5BaMSi_4O_{12}$, is also evident from the X-ray diffraction patterns. Relatively large amounts of this particular impurity phase do not significantly reduce the ionic conductivity because this impurity phase is also ionically conductive. The $Na_3BaGdSi_4O_{12}$ has a conductivity of $6 \times 10^{-4}$ (ohm cm)$^{-1}$ at 200° C and $3 \times 10^{-3}$ (ohm cm)$^{-1}$ at 300° C. The $Na_3BaYSi_4O_{12}$ has a conductivity of $1 \times 10^{-3}$ (ohm cm)$^{-1}$ at 200° C and $3 \times 10^{-3}$ (ohm cm)$^{-1}$ at 300° C.

Additions of up to 20 mole percent $Na_2Si_2O_5$ to the conductive $Na_5MSi_4O_{12}$ phases are effective in significantly raising the conductivity. The amorphous glass $Na_2Si_2O_5$ has been discovered to be a good $Na^+$ conductor with conductivities of $5 \times 10^{-5}$ (ohm cm)$^{-1}$ at 200° C and $6.5 \times 10^{-4}$ (ohm cm)$^{-1}$ at 300° C. Since $Na_2Si_2O_5$ forms a stable glass at 874° C and is ionically conductive, the improvement in conductivity is believed to result from the presence of amorphous $Na_2Si_2O_5$ between the grains of $Na_5MSi_4O_{12}$. The $Na_2Si_2O_5$ increases the contact between grains and also acts as a sintering aid.

The novel compositions of this invention are used as ionic conductors which pass currents of $Na^+$. These compositions can be used in high-energy density storage batteries which usually operate at elevated temperatures with molten Na as the anode source of sodium ions. Illustrative cathodes for such batteries are liquid sulfur, selenium, or tellurium which serve to remove the sodium ions by forming a composition approaching $Na_2S_4$, or the equivalent selenium or tellurium compound.

The compositions can also be used in low drain, low power density primary batteries including completely solid state primary batteries. FIG. 2 shows a primary battery with electrolyte. The anode 2 for such batteries can consist of Na metal, sodium-amalgam, or sodium tungsten bronzes; the cathode 4 may be $V_2O_5$, bromine, $TiS_2$ or similar materials which react with and thereby remove the Na transmitted through the solid electrolyte 1. Connector electrodes 3 and 5 make an electrical circuit between the $Na^+$ supplying anode and the $Na^+$ removing cathode. An all-solid cell is encapsulated to prevent reaction of the components with the atmosphere. Completely solid state cells offer the advantages of long shelf life, broad temperature range of operability and miniaturization.

Figure 6:
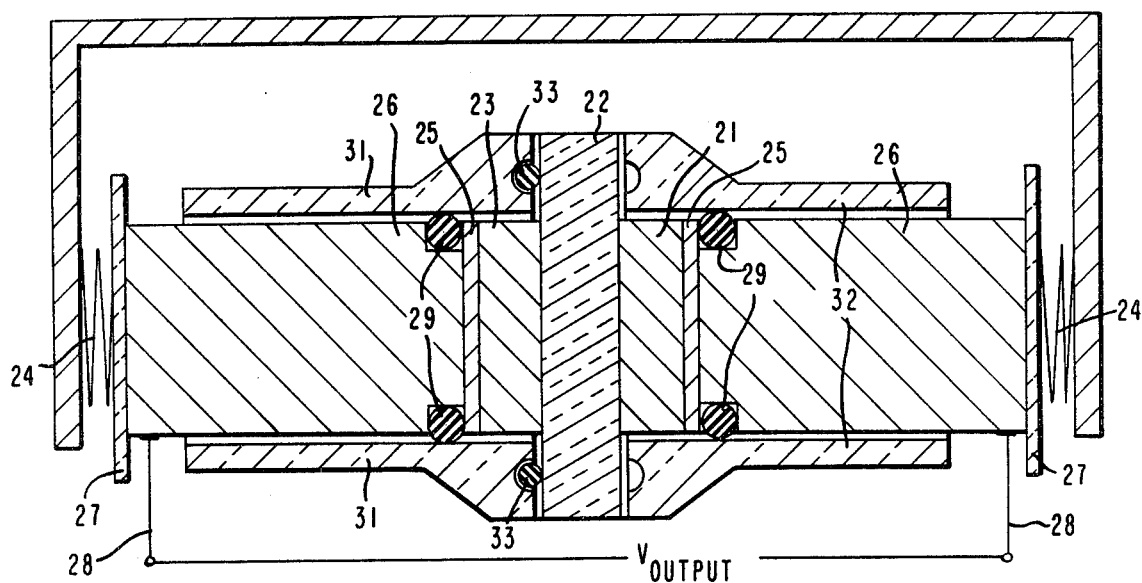
FIG. 6 is an illustrative, cross-sectional view of a sodium-titanium sulfide voltaic cell.

Other illustrative batteries are shown in FIGS. 4 and 6 which are more fully described in Examples 48 and 49.

For electrowinning of sodium metal, the anode can consist of a carbon electrode situated in a dissociable molten salt such as $NaCl-AlCl_3$. $Na^+$ ions are electrically transported from the molten salt through the solid electrolyte of one of the instant compositions and converted to elemental sodium at the cathode. An illustrative cell is shown in FIG. 3 which is more fully described in Example 46.

For purifying of sodium, the anode consists of an inert connecting electrode situated in a molten alloy, such as sodium amalgam or other source of impure sodium. Sodium ions are produced at the anode and are electrically attracted through a solid electrolyte of one of the instant compositions. The ions are then deposited at the cathode as pure elemental sodium.

Other devices in which these electrolytes can be used, e.g., coulometers, timers, etc. will be obvious to those skilled in the art.

EMBODIMENTS OF THE INVENTION

The following examples illustrate the preparation of the sodium rare earth silicate and germanate compositions of this invention and their use as solid electrolytes.

EXAMPLE 1

A mixture of 1.930 g $Na_2CO_3$, 1.320 g $Gd_2O_3$, and 1.750 g $SiO_2$ was ground in a mortar, heated in a platinum crucible at 500° C for 4 hr, 700° C for 4 hr, and 900° C for 4 hr. The product was reground and reheated at 1000° C for 16 hr. The Pt crucible containing this product was quenched in a water bath. The product was reground in an agate ball mill for 2 hr, reheated at 900° C for 16 hr and quenched again in a water bath. The powder product $Na_5GdSi_4O_{12}$ gave a single phase X-ray diffraction pattern characteristic of the rhombohedral structure as shown in Table I. Hexagonal cell dimensions obtained from an analysis of this data are $a = 22.13A$, $c = 12.65A$, and unit cell volume $= 5363 A^3$. (For convenience, the hexagonal cell dimensions and ionic conductivities of all examples are summarized in Table II).

A sample was prepared in the form of a disc 0.66 cm $\times$ 1.08 cm diameter with a density of 3.02 g/cc by pressing the powder product in a steel die at an approximate pressure of 30,000 psi, heating the disc to a temperature of 900° C for 16 hr and rapidly cooling in air. The sample disc was mounted in a stainless steel holder between two discs of Na foil 0.015 inch thick supported on Ni screens. The sample temperature was raised above the melting point of Na metal to assure good contact. The a-c conductance was measured using a Wayne-Kerr universal bridge at a frequency of $10^4$ radians/sec. The sample showed a conductivity of $8 \times 10^{-2} (\Omega \text{ cm})^{-1}$ at 200° C with a temperature dependence indicated in FIG. 1. The d-c conductivity was checked by applying slowly varying voltages (triangular wave forms with a frequency less than 0.01 Hz) and recording the current. The D.C. conductivity was calculated from the current voltage plot. Excellent agreement with the a-c results were obtained. Upon removal of the sample, the Na was cleaned from the faces, and no apparent attack by the molten Na was evident.

TABLE I

| X-ray Diffraction Patterns of $Na_5GdSi_4O_{12}$ And $Na_5DySi_4O_{12}$ | | | | | | | | |
|---|---|---|---|---|---|---|---|---|
| $Na_5GdSi_4O_{12}$ | | | | | $Na_5DySi_4O_{12}$ | | | |
| Reflection | | | d Spacings Observed | Intensity Observed | Reflection | | | d Spacings Observed | Intensity Observed |
| h | k | l | | | h | k | l | | |
| 1 | 1 | 0 | 10.962 | 15 | 1 | 1 | 0 | 11.089 | 10 |
| 2 | 1 | 1 | 6.258 | 90 | 2 | 1 | 1 | 6.276 | 95 |
| 0 | 1 | 2 | 5.981 | 10 | 0 | 1 | 2 | 6.011 | 5 |
| 2 | 2 | 0 | 5.514 | 50 | 2 | 2 | 0 | 5.521 | 60 |
| 2 | 0 | 2 | 5.257 | 10 | 2 | 0 | 2 | 5.266 | 5 |
| 4 | 1 | 0 | 4.173 | 40 | 4 | 1 | 0 | 4.166 | 50 |
| 3 | 2 | 1 | 4.143 | 40 | 3 | 2 | 1 | 4.142 | 45 |
| 3 | 1 | 2 | 4.062 | 65 | 3 | 1 | 2 | 4.060 | 60 |
| 1 | 1 | 3 | 3.937 | 50 | 1 | 1 | 3 | 3.934 | 60 |
| 0 | 4 | 2 | 3.813 | 5 | 5 | 1 | 1 | 3.310 | 40 |
| 5 | 1 | 1 | 3.316 | 50 | 5 | 0 | 2 | 3.273 | 5 |
| 5 | 0 | 2 | 3.276 | 10 | 6 | 0 | 0 | 3.182 | 35 |

TABLE I-continued

X-ray Diffraction Patterns of $Na_5GdSi_4O_{12}$ And $Na_5DySi_4O_{12}$

| $Na_5GdSi_4O_{12}$ | | | | | $Na_5DySi_4O_{12}$ | | | | |
|---|---|---|---|---|---|---|---|---|---|
| Reflection | | | d Spacings | Intensity | Reflection | | | d Spacings | Intensity |
| h | k | l | Observed | Observed | h | k | l | Observed | Observed |
| 6 | 0 | 0 | 3.189 | 40 | 5 | 2 | 0 | 3.058 | 10 |
| 5 | 2 | 0 | 3.066 | 10 | 4 | 3 | 1 | | |
| 4 | 3 | 1 | | | 0 | 2 | 4 | 2.997 | 25 |
| 0 | 2 | 4 | 3.002 | 40 | 4 | 1 | 3 | 2.959 | 10 |
| 1 | 5 | 2 | | | 2 | 1 | 4 | 2.893 | 10 |
| 4 | 1 | 3 | 2.967 | 15 | 1 | 6 | 1 | 2.836 | 10 |
| 2 | 1 | 4 | 2.895 | 10 | 3 | 4 | 2 | 2.812 | 10 |
| 1 | 6 | 1 | 2.844 | 20 | 4 | 4 | 0 | 2.757 | 100 |
| 3 | 4 | 2 | 2.816 | 25 | 1 | 3 | 4 | 2.712 | 40 |
| 4 | 4 | 0 | 2.765 | 100 | 4 | 0 | 4 | 2.634 | 50 |
| 1 | 3 | 4 | 2.718 | 40 | 0 | 1 | 5 | 2.503 | 10 |
| 4 | 0 | 4 | 2.638 | 50 | 5 | 3 | 2 | 2.474 | 20 |
| 7 | 1 | 0 | 2.529 | 10 | 5 | 2 | 3 | | |
| 6 | 0 | 3 | | | 0 | 5 | 4 | 2.436 | 15 |
| 5 | 3 | 2 | 2.510 | 25 | 2 | 0 | 5 | | |
| 0 | 1 | 5 | | | 2 | 6 | 2 | | |
| 5 | 2 | 3 | 2.480 | 40 | 1 | 2 | 5 | 2.383 | 15 |
| 2 | 6 | 2 | 2.450 | 20 | 2 | 4 | 4 | | |
| 2 | 0 | 5 | | | 2 | 7 | 1 | 2.294 | 20 |
| 0 | 5 | 4 | 2.439 | 25 | 2 | 3 | 5 | 2.188 | 10 |
| 6 | 3 | 0 | 2.415 | 10 | 7 | 6 | 1 | 2.188 | 40 |
| 5 | 4 | 1 | | | 6 | 3 | 3 | 2.090 | 5 |
| 1 | 2 | 5 | 2.389 | 25 | 8 | 2 | 0 | | |
| 2 | 4 | 4 | | | 7 | 0 | 4 | 2.066 | 20 |
| 2 | 7 | 1 | 2.301 | 35 | 1 | 1 | 6 | | |
| 4 | 0 | 2 | | | 4 | 2 | 5 | | |
| 8 | 0 | 2 | 2.240 | 35 | 6 | 4 | 2 | | |
| 0 | 4 | 5 | | | 6 | 2 | 4 | 2.032 | 10 |
| 2 | 3 | 5 | 2.192 | 25 | 3 | 7 | 2 | 1.999 | 10 |
| 7 | 3 | 1 | 2.124 | 25 | 3 | 0 | 6 | | |
| 0 | 0 | 6 | 2.108 | 10 | 6 | 5 | 1 | 1.977 | 35 |
| 5 | 0 | 5 | | | 7 | 4 | 0 | | |
| 1 | 8 | 2 | | | 0 | 8 | 4 | 1.905 | 40 |
| 6 | 3 | 3 | 2.096 | 10 | 6 | 1 | 5 | | |
| 8 | 2 | 0 | | | 9 | 1 | 2 | | |
| 1 | 1 | 6 | 2.071 | 35 | 4 | 1 | 6 | 1.878 | 5 |
| 7 | 0 | 4 | | | 2 | 7 | 4 | | |
| 4 | 2 | 5 | | 8 | 0 | 7 | 5 | 1.853 | 20 |
| 6 | 4 | 2 | | | 3 | 2 | | | |
| 3 | 7 | 2 | 2.038 | 15 | 8 | 1 | 4 | 1.825 | 20 |
| 6 | 2 | 4 | | | 3 | 3 | 6 | | |
| 3 | 0 | 6 | 2.004 | 10 | 2 | 6 | 5 | | |
| 6 | 5 | 1 | 1.983 | 40 | 0 | 10 | 2 | | |
| | | | | | 4 | 6 | 4 | 1.802 | 15 |

The strongest line is arbitrarily assigned an intensity of 100.

TABLE II

HEXAGONAL CELL DIMENSIONS AND IONIC CONDUCTIVITIES OF EXPERIMENTAL COMPOSITIONS

| Example No. | Composition | a, Å | c, Å | V, Å$^3$ | Conductivity $\sigma$(200° C) ($\Omega$ cm)$^{-1}$ |
|---|---|---|---|---|---|
| 1 | $Na_5GdSi_4O_{12}$ | 22.13 | 12.65 | 5363 | $8 \times 10^{-2}$ |
| 2 | $Na_5SmSi_4O_{12}$ | 22.16 | 12.66 | 5386 | $1 \times 10^{-1}$ |
| 3 | $Na_5DySi_4O_{12}$ | 22.06 | 12.62 | 5319 | $3.2 \times 10^{-2}$ |
| 4 | $Na_5HoSi_4O_{12}$ | 22.03 | 12.61 | 5301 | $5.6 \times 10^{-2}$ |

TABLE II-continued
HEXAGONAL CELL DIMENSIONS AND IONIC CONDUCTIVITIES OF EXPERIMENTAL COMPOSITIONS

| Example No. | Composition | a,A | c,A | V,A$^3$ | Conductivity $\sigma(200°$ C$)$ $(\Omega$ cm$)^{-1}$ |
|---|---|---|---|---|---|
| 5 | $Na_5TbSi_4O_{12}$ | 22.08 | 12.63 | 5332 | $6.6 \times 10^{-2}$ |
| 6 | $Na_5YSi_4O_{12}$ | 22.05 | 12.61 | 5307 | $3.9 \times 10^{-2}$ |
| Control | $Na_5ScSi_4O_{12}$ | 21.67 | 12.44 | 5058 | $4.5 \times 10^{-4}$ |
| 7 | $Na_5LuSi_4O_{12}$ | 21.94 | 12.56 | 5235 | $8 \times 10^{-3}$ |
| 8 | $Na_5ErSi_4O_{12}$ | 22.01 | 12.60 | 5284 | |
| 9 | $Na_5YbSi_4O_{12}$ | 21.94 | 12.57 | 5239 | $8 \times 10^{-3}$ |
| 10 | $Na_5TmSi_4O_{12}$ | 21.96 | 12.58 | 5252 | $9 \times 10^{-3}$ |
| 11 | $Na_5Gd_8Nd_2Si_4O_{12}$ | 22.17 | 12.66 | 5388 | $6.0 \times 10^{-2}$ |
| 12 | $Na_5Gd_6Nd_4Si_4O_{12}$ | 22.17 | 12.68 | 5396 | $5.0 \times 10^{-2}$ |
| 13 | $Na_5Gd_4Nd_6Si_4O_{12}$ | 22.18 | 12.68 | 5402 | $1.9 \times 10^{-2}$ |
| 14 | $Na_5Gd_8Pr_2Si_4O_{12}$ | 22.16 | 16.67 | 5385 | $3.4 \times 10^{-2}$ |
| 15 | $Na_5Gd_6Pr_4Si_4O_{12}$ | 22.13 | 12.70 | 5386 | $3.8 \times 10^{-2}$ |
| 16 | $Na_5Gd_8La_2Si_4O_{12}$ | 22.15 | 12.66 | 5378 | $5.0 \times 10^{-2}$ |
| 17 | $Na_{4.9}Gd_9Zr_{.1}Si_4O_{12}$ | 22.12 | 12.63 | 5348 | $1.0 \times 10^{-1}$ |
| 18 | $Na_{4.8}Gd_8Zr_{.2}Si_4O_{12}$ | 22.12 | 12.63 | 5352 | $5.5 \times 10^{-2}$ |
| 19 | $Na_{4.7}Gd_7Zr_{.3}Si_4O_{12}$ | 22.10 | 12.62 | 5340 | $2.8 \times 10^{-2}$ |
| 20 | $Na_{4.9}Gd_7Nd_2Zr_{.1}Si_4O_{12}$ | 22.17 | 12.63 | 5375 | $8.6 \times 10^{-2}$ |
| 21 | $Na_{4.9}GdSi_{3.9}P_{.1}O_{12}$ | 22.14 | 12.65 | 5371 | $4.5 \times 10^{-2}$ |
| 22 | $Na_{4.9}GdSi_{3.95}S_{.05}O_{12}$ | 22.15 | 12.65 | 5376 | $7.0 \times 10^{-2}$ |
| 23 | $Na_{4.8}GdSi_{3.9}S_{.1}O_{12}$ | 22.14 | 12.66 | 5373 | $4.0 \times 10^{-2}$ |
| 24 | $Na_5GdSi_3GeO_{12}$ | 22.28 | 12.72 | 5472 | $5.2 \times 10^{-2}$ |
| 25 | $Na_5GdSi_2Ge_2O_{12}$ | 22.45 | 12.82 | 5596 | $1.1 \times 10^{-2}$ |
| 26 | $Na_5GdGe_4O_{12}$ | 22.78 | 12.99 | 5840 | |
| 27 | $Na_5Sm_{.5}Nd_{.5}Si_4O_{12}$ | 22.18 | 12.68 | 5404 | |
| 28 | $Na_5Sm_8Pr_2Si_4O_{12}$ | 22.19 | 12.67 | 5404 | |
| 29 | $Na_{4.7}Y_7Zr_3Si_4O_{12}$ | 21.99 | 12.58 | 5271 | $2.0 \times 10^{-2}$ |
| 30 | $Na_{4.7}Y_7Hf_3Si_4O_{12}$ | 22.00 | 12.58 | 5269 | $2.6 \times 10^{-2}$ |
| 31 | $Na_{4.95}Y_{.95}Th_{.05}Si_4O_{12}$ | 22.04 | 12.60 | 5304 | $3.2 \times 10^{-2}$ |
| 32 | $Na_{4.8}Y_6Nd_2Zr_2Si_4O_{12}$ | 22.03 | 12.58 | 5289 | $4 \times 10^{-2}$ |
| 33 | $Na_{4.9}Y_5Nd_4Zr_1Si_4O_{12}$ | 22.10 | 12.63 | 5339 | $4 \times 10^{-2}$ |
| 34 | $Na_5GdSi_4O_{12}$ + 10% $Na_2Si_2O_5$ | | | | $1.2 \times 10^{-1}$ |
| 35 | $Na_5GdSi_4O_{12}$ + $Na_3BaGdSi_4O_{12}$ | | | | $7.0 \times 10^{-2}$ |
| 36 | $Na_5GdSi_4O_{12}$ + $Na_3BaGdSi_4O_{12}$ | | | | $3.0 \times 10^{-2}$ |
| 37 | $Na_5YSi_4O_{12}$ + $Na_3BaYSi_4O_{12}$ | | | | $2.5 \times 10^{-2}$ |
| 38 | $Na_5TbGe_4O_{12}$ | 22.74 | 12.97 | 5808 | $1.6 \times 10^{-3}$ |
| 39 | $Na_5YGe_4O_{12}$ | 22.62 | 12.95 | 5735 | |
| 40 | $Na_5LuGe_4O_{12}$ | 22.58 | 12.90 | 5697 | |
| 41 | $Na_5YbGe_4O_{12}$ | 22.61 | 12.92 | 5718 | |
| 42 | $Na_5TmGe_4O_{12}$ | 22.63 | 12.92 | 5718 | |
| 42 | $Na_5TmGe_4O_{12}$ | 22.63 | 12.92 | 5734 | $7.6 \times 10^{-3}$ |
| 43 | $Na_5ErGe_4O_{12}$ | 22.67 | 12.95 | 5763 | |
| 44 | $Na_5HoGe_4O_{12}$ | 22.68 | 12.96 | 5770 | $6.9 \times 10^{-3}$ |
| 45 | $Na_5DyGe_4O_{12}$ | 22.72 | 12.97 | 5795 | $2.8 \times 10^{-3}$ |

EXAMPLE 2

A mixture of 1.949 g $Na_2CO_3$, 1.283 g $Sm_2O_3$ and 1.768 g $SiO_2$ was ground in a mortar, heated in a platinum crucible at 500° C for 4 hr, and 900° C for 16 hr. The product was ground in a Geoscience agate planetary ball mill for 2 hr, reheated in a platinum crucible at 900° C for 31 hr, and quenched in a water bath. The product $Na_5SmSi_4O_{12}$ gave a single phase diffraction pattern characteristic of the rhombohedral structure and similar to those shown in Table I with hexagonal cell dimensions $a = 22.16$ A, $c = 12.66$ A and unit cell volume $= 5386$ A$^3$. A disc prepared by the technique described in Example 1 showed a conductivity of $1 \times 10^{-1}$ $(\Omega$ cm$)^{-1}$ at 200° C with a temperature dependence indicated in FIG. 1.

EXAMPLE 3

A mixture of 1.915 g $Na_2CO_3$, 1.348 g $Dy_2O_3$, and 1.737 g $SiO_2$ was ground in a mortar, heated in a platinum crucible at 500° C for 4 hr, and 1000° C for 4 hr. The product was reground in an agate ball mill, heated at 800° C for 16 hr, 1000° C for 16 hr, and quenched in a water bath. The product $Na_5DySi_4O_{12}$ gave a single phase X-ray diffraction pattern characteristic of the rhombohedral structure as shown in Table I. Hexagonal cell dimensions obtained from an analysis of this data are $a = 22.06$ A, $c = 12.62$ A, and unit cell volume $= 5319$ A$^3$. A disc prepared by the technique described in Example 1 and heated at 1000° C for 24 hr showed a conductivity of $3.2 \times 10^{-2}$ $(\Omega$ cm$)^{-1}$ at 200° C with a temperature dependence indicated in FIG. 1.

EXAMPLE 4

A mixture of 1.908 g $Na_2CO_3$, 1.361 g $Ho_2O_3$ and 1.731 g $SiO_2$ was ground in a mortar, heated in a Pt crucible at 500° C for 4 hr and 1000° C for 4 hr. This product was ground in a planetary ball mill for 2 hr, heated at 800° C for 16 hr, 1000° C for 16 hr and quenched in a water bath. The product $Na_5HoSi_4O_{12}$ gave a single phase diffraction pattern characteristic of the rhombohedral structure and similar to those shown in Table I. Hexagonal cell dimensions are $a = 22.03$ A, $c = 12.61$ A and $V = 5301$ A$^3$. A disc prepared by the technique described in Example 1 and heated at 1000° C for 24 hr showed a conductivity of $5.6 \times 10^{-2}$ $(\Omega$ cm$)^{-1}$ at 200° C.

EXAMPLE 5

A mixture of 1.925 g $Na_2CO_3$, 1.329 g $Tb_2O_3$ and 1.746 g $SiO_2$ was ground in a mortar, heated in a Pt crucible at 500° C for 4 hr and 1000° C for 4 hr. This product was ground in a planetary ball mill for 2 hr, heated at 800° C for 16 hr, 1000° C for 16 hr and quenched in a water bath. The product $Na_5TbSi_4O_{12}$ gave a single phase diffraction pattern characteristic of the rhombohedral structure and similar to those shown in Table I. Hexagonal cell dimensions are $a = 22.08$ A, $c = 12.63$ A and $V = 5332$ A$^3$. A disc prepared by the technique described in Example 1 and heated at 1000° C for 24 hr showed a conductivity of $6.6 \times 10^{-2}$ ($\Omega$ cm)$^{-1}$ at 200° C.

EXAMPLE 6

A mixture of 4.200 g NaHCO$_3$, 2.403 g SiO$_2$ and 1.129 g Y$_2$O$_3$ obtained from the decomposition of Y$_2$(CO$_3$)$_3$ at 600° C was ball-milled and fired in a platinum crucible to 1120° C for 16 hr. X-ray analysis showed the product Na$_5$YSi$_4$O$_{12}$ to be single-phase with hexagonal cell dimensions $a$ = 22.05 A, $c$ = 12.61 A, and unit cell volume = 5307 A$^3$. The X-ray diffraction pattern was similar to those shown in Table I. A portion of the product was pressed into a ½ inch disc at ~60,000 psi and sintered at 1000° C for 60 hr. The disc weighed 0.908 g with dia = 1.24 cm and length = 0.325 cm and the calculated density was 2.31 g/cm$^3$ corresponding to 82% of theoretical density.

The sample disc was mounted in a stainless steel holder between two discs of Na foil 0.015 inch thick supported on Ni screens. The sample temperature was raised above the melting point of Na metal to assure good contact. The a-c conductance was measured using a Wayne-Kerr universal bridge at a frequency of 10$^4$ radians/sec. The sample showed a conductivity of $3.9 \times 10^{-2}$ ($\Omega$-cm)$^{-1}$ at 200° C with a temperature dependence indicated in FIG. 1. The d-c conductivity was checked by applying slowly varying voltages (triangular wave forms with a frequency less than 0.01 Hz) and recording the current. Excellent agreement with the a-c results were obtained. Upon removal of the sample, the Na was cleaned from the faces, and no apparent attack by the molten Na was evident.

CONTROL EXAMPLE

A mixture of 2.307 g Na$_2$CO$_3$, 0.600 g Sc$_2$O$_3$, and 2.092 g SiO$_2$ was ground in a mortar and heated in a platinum crucible at 500° C for 4 hr, and 1000° C for 4 hr. This mixture was reground, heated at 1000° C for 16 hr and quenched in a water bath. The X-ray diffraction pattern using a Hagg-Guinier camera from this Na$_5$ScSi$_4$O$_{12}$ product was similar to those shown in Table I and indicated a rhombohedral structure with hexagonal cell dimensions $a$ = 21.67 A, $c$ = 12.44 A, and unit cell volume = 5058 A$^3$. The conductivity of a disc prepared as in Example 1 and heated at 1000° C for 4 hr was only $4.5 \times 10^{-4}$ ($\Omega$-cm)$^{-1}$ at 200° C with a temperature dependence indicated in FIG. 1.

EXAMPLES 7-10

Examples 7-10 were all prepared according to the procedure outlined in the Control Example using the mixture of starting materials shown in Table III. The powder products all gave single phase X-ray patterns characteristic of the rhombohedral structure and similar to those shown in Table I and the hexagonal unit cell dimensions and volume are shown in Table III. Discs of these samples were prepared as described in Example 1. The conductivities at 200° C are listed in Table III and the temperature dependence of the samples of the Na$_5$LuSi$_4$O$_{12}$, Na$_5$YbSi$_4$O$_{12}$ and Na$_5$TmSi$_4$O$_{12}$ products is indicated in FIG. 1.

TABLE III

| Example No | Product | Reactants Na$_2$CO$_3$ | SiO$_2$ | Other | Hexagonal Unit Cell Parameters a(A) | c(A) | V(A$^3$) | Ionic Conductivity at 200° C ($\Omega$ cm)$^{-1}$ |
|---|---|---|---|---|---|---|---|---|
| 7 | Na$_5$LuSi$_4$O$_{12}$ | 1.881g | 1.706g | 1.413g Lu$_2$O$_3$ | 21.94 | 12.56 | 5235 | $8 \times 10^{-3}$ |
| 8 | Na$_5$ErSi$_4$O$_{12}$ | 1.902g | 1.725g | 1.373g Er$_2$O$_3$ | 22.01 | 12.60 | 5284 | |
| 9 | Na$_5$YbSi$_4$O$_{12}$ | 1.886g | 1.711g | 1.403g Yb$_2$O$_3$ | 21.94 | 12.57 | 5239 | $8 \times 10^{-3}$ |
| 10 | Na$_5$TmSi$_4$O$_{12}$ | 1.898g | 1.721g | 1.382g Tm$_2$O$_3$ | 21.96 | 12.58 | 5252 | $9 \times 10^{-3}$ |

EXAMPLE 11

A mixture of 1.937 g Na$_2$CO$_3$, 1.060 g Gd$_2$O$_3$, 0.246 g Nd$_2$O$_3$ and 1.757 g SiO$_2$ was ground in a mortar, heated in a Pt crucible at 500° C for 4 hr, 1000° C for 4 hr, 800° C for 64 hr. The product was ball milled in an agate planetary mill for 2 hr, heated at 900° C for 16 hr, quenched in a water bath, ball milled again for 2 hr, heated at 950° C for 4 hr, and quenched in a water bath. The powder product was single phase crystalline Na$_5$Gd$_{.8}$Nd$_{.2}$Si$_4$O$_{12}$ with an X-ray diffraction pattern similar to those shown in Table I and with hexagonal dimensions $a$ = 22.17 A, $c$ = 12.66 A, and V = 5388 A$^3$. A disc prepared by the technique in Example 1 and heated at 1000° C for 24 hr was used to measure the ionic conductivity. The conductivity at 200° C was $6.0 \times 10^{-2}$ ($\Omega$ cm)$^{-1}$.

EXAMPLE 12

A mixture of 1.944 g Na$_2$CO$_3$, 0.748 g Gd$_2$O$_3$, 0.494 g Nd$_2$O$_3$ and 1.764 g SiO$_2$ was ground in a mortar, heated in a Pt crucible at 500° C for 4 hr, 1000° C for 1 hr, 800° C for 64 hr. The product was ball milled in an agate planetary mill for 2 hr, heated at 900° C for 16 hr, quenched in a water bath, ball milled again for 2 hr, heated at 950° C for 4 hr and quenched in a water bath. The product was single phase crystalline Na$_5$Gd$_{.6}$Nd$_{.4}$Si$_4$O$_{12}$ with an X-ray diffraction pattern similar to those shown in Table I and with hexagonal cell dimensions $a$ = 22.17 A, $c$ = 12.68 A, and V = 5396 A$^3$. A disc prepared by the technique of Example 1 and heated at 1000° C for 24 hr was used to measure the ionic conductivity. The conductivity at 200° C was $5.0 \times 10^{-2}$ ($\Omega$ cm)$^{-1}$.

EXAMPLE 13

A mixture of 1.952 g Na$_2$CO$_3$, 0.534 g Gd$_2$O$_3$, 0.744 g Nd$_2$O$_3$ and 1.770 g SiO$_2$ was ground in a mortar, heated in a Pt crucible at 500° C for 4 hr, 1000° C for 41 hr, 800° C for 64 hr. The product was ball milled in an agate planetary mill for 2 hr, heated at 900° C for 16 hr, quenched in a water bath, ball milled again for 2 hr, heated at 950° C for 4 hr and quenched, reheated at 1000° C for 24 hr, quenched, reheated at 800° C for 64 hr, ball milled, reheated to 1000° C for 16 hr and quenched. The product was single phase crystalline Na$_5$Gd$_{.4}$Nd$_{.6}$Si$_4$O$_{12}$ with an X-ray diffraction pattern similar to those shown in Table I and with hexagonal cell dimensions $a$ = 22.18 A, $c$ = 12.68 A and V = 5401 A$^3$. A disc prepared by the technique of Example 1 and heated to 1000° C for 24 hr was used to measure the ionic conductivity. The conductivity at 200° C was 1.9 × 10$^{-2}$ ($\Omega$ cm)$^{-1}$.

EXAMPLE 14

A mixture of 1.935 g $Na_2CO_3$, 1.059 g $Gd_2O_3$, 0.250 g $Pr_6O_{11}$ and 1.755 g $SiO_2$ was ground in a mortar, heated in a Pt crucible to 500° C for 16 hr, and 1000° C for 4 hr. The product was ground in an agate planetary ball mill for 2 hr, heated to 900° C for 16 hr and quenched in a water bath. This product was ball milled again for 2 hr, heated at 950° C for 4 hr and quenched in a water bath. The single phase crystalline $Na_5Gd_{.8}Pr_{.2}Si_4O_{12}$ gave an X-ray diffraction pattern similar to those shown in Table I with hexagonal cell dimensions $a = 22.16$ A, $c = 12.67$ A and $V = 5385$ A$^3$. A disc prepared by the technique of Example 1 and heated to 1000° C for 24 hr had an ionic conductivity at 200° C of 3.4 × 10$^{-2}$ ($\Omega$ cm)$^{-1}$.

EXAMPLE 15

A mixture of 1.943 g $Na_2CO_3$, 0.797 g $Gd_2O_3$, 0.498 g $Pr_6O_{11}$ and 1.762 g $SiO_2$ was ground in a mortar, heated in a Pt crucible to 500° C for 16 hr, and 1000° C for 4 hr. The product was ground in an agate planetary ball mill for 2 hr, heated to 900° C for 86 hr and quenched in a water bath. This product was ball milled again for 2 hr, heated at 950° C for 4 hr and quenched in a water bath. The single phase crystalline $Na_5Gd_{.6}Pr_{.4}Si_4O_{12}$ gave an X-ray diffraction pattern similar to those shown in Table I with hexagonal cell dimensions $a = 22.13$ A, $c = 12.70$ A and $V = 5386$ A$^3$. A disc prepared as in Example 14 had an ionic conductivity at 200° C of 3.8 × 10$^{-2}$ ($\Omega$ cm)$^{-1}$.

EXAMPLE 16

A mixture was made of 7.761 g $Na_2CO_3$, 7.038 g $SiO_2$, 4.247 g $Gd_2O_3$ and 0.954 g $La_2O_3$. Both rare earth oxides were obtained by the decomposition of the corresponding carbonates at 650° C. The mixture was heated in a Pt crucible at 500° C for 16 hr and 1000° C for 4 hrs. The product was milled in a planetary agate ball-mill for 4 hr and heated to 900° C for 16 hr before being quenched in a water bath. The procedure of milling and firing was repeated again. The product $Na_5Gd_{.8}La_{.2}Si_4O_{12}$ gave an X-ray diffraction pattern similar to those shown in Table I. X-ray Analysis of this data showed the product to be essentially single phase, with hexagonal cell dimensions $a = 22.15$ A, $c = 12.66$ A, and $V = 5378$ A$^3$. A portion of this sample was pressed into a ½ inch disc at ~60,000 psi and sintered at 900° C for 16 hr. The disc weighed 2.44 g, with dia = 1.13 cm and length = 0.80 cm. The calculated density was 3.03 g/cm$^3$, corresponding to 95% of the theoretical density. The conductivity was 5 × 10$^{-2}$ ($\Omega$ cm)$^{-1}$ at 200° C.

EXAMPLES 17–19

Each of these three examples was prepared in the following manner. The quantities of $Na_2CO_3$, $Gd_2O_3$, $ZrO_2$ and $SiO_2$ shown in Table IV were ground in a mortar, placed in a platinum crucible and heated to 600° C for 16 hr, 800° C for 3 hr, 1000° C for 16 hr and quenched in air. The sintered powder was ball-milled in an agate mill for 1 hr, reheated to 900° C for 16 hr and quenched in air. The powder was single phase and had a characteristic X-ray pattern similar to those shown in Table I (indicative of a rhombohedral cell) with the hexagonal cell parameters shown in Table IV. A portion of each powder was pressed into a disc at 60,000 psi and then heated to 950° C for 16 hr, furnace cooled to 200° C and quenched. The ionic conductivity of the discs were measured and the conductivity at 200° C given in Table IV.

TABLE IV

| Example No. | Product | Reactants | | | | Hexagonal Unit Cell Parameters | | | Ionic Conductivity at 200° C ($\Omega$ cm$^{-1}$) |
|---|---|---|---|---|---|---|---|---|---|
| | | $Na_2CO_3$ | $Gd_2O_3$ | $ZrO_2$ | $SiO_2$ | a(A) | c(A) | V(A$^3$) | |
| 17 | $Na_{4.9}Gd_{.9}Zr_{.1}Si_4O_{12}$ | 2.287g | 1.437g | 0.109g | 2.117g | 22.12 | 12.63 | 5348 | 1 × 10$^{-1}$ |
| 18 | $Na_{4.8}Gd_{.8}Zr_{.2}Si_4O_{12}$ | 2.276g | 1.298g | 0.221g | 2.151g | 22.12 | 12.63 | 5352 | 5.5 × 10$^{-2}$ |
| 19 | $Na_{4.7}Gd_{.7}Zr_{.3}Si_4O_{12}$ | 2.265g | 1.154g | 0.336g | 2.185g | 22.10 | 12.62 | 5340 | 2.8 × 10$^{-2}$ |

EXAMPLE 20

An intimate mixture of 2.298 g $Na_2CO_3$, 1.123 g $Gd_2O_3$, 0.298 g $Nd_2O_3$, 0.109 g $ZrO_2$ and 2.127 g $SiO_2$ was heated to 1000° C for 16 hr, 800° C for 20 hr, 500° C for 6 hr, 1050° C for 8 hr, 800° C for 5 hr, and allowed to cool with the furnace. The product was then ball milled in an agate planetary mill for 1 hr. A portion of the resulting powder was pressed into a ½ inch disc at 36,000 psi, and then heated to 500° C for 4 hr, 800° C for 2½ hr, 1000° C for 15½ hr and allowed to cool with the furnace. The resulting disc had a density corresponding to about 95% of its theoretical value. The conductivity was measured using sodium metal electrodes and had a value of 8.6 × 10$^{-2}$ (ohm cm)$^{-1}$ at 200° C. The product was single phase $Na_{4.9}Gd_{.7}Nd_{.2}Zr_{.1}Si_4O_{12}$ with an X-ray pattern similar to those shown in Table I and with hexagonal cell constants $a = 22.17$ A, $c = 12.63$ A and $V = 5375$ A$^3$.

EXAMPLE 21

A mixture of 1.891 g $Na_2CO_3$, 1.315 g $Gd_2O_3$, 1.706 g $SiO_2$ and 0.084 g $NH_4H_2PO_4$ was ground in an agate mortar, heated in a Pt crucible at 200° C for 1 hr, 400° C for 1 hr, 500° C for 4 hr and 1000° C for 4 hr. The product was ball milled in a planetary agate mill for 2 hr, heated at 900° C for 16 hr and quenched in a water bath. The product was crystalline and corresponded to the nominal formula $Na_{4.9}GdSi_{3.9}P_{0.1}O_{12}$ with a trace of an unidentified phase, based on the X-ray diffraction pattern which was similar to those shown in Table I. The cell dimensions of the hexagonal phase were $a = 22.14$ A, $c = 12.65$ A and $V = 5371$ A$^3$. The conductivity at 200° C of a sintered disc prepared by the technique of Example 1 and heated to 1000° C for 24 hr was 4.5 × 10$^{-2}$ ($\Omega$ cm)$^{-1}$.

EXAMPLE 22

A mixture of 1.870 g $Na_2CO_3$, 1.333 g $Gd_2O_3$, 1.745 g $SiO_2$ and 0.052 g $Na_2SO_4$ was ground in a mortar and heated in a Pt crucible at 500° C for 4 hr and 1000° C for 4 hr. The product was ground in an agate planetary ball-mill for 2 hr, heated at 900° C for 16 hr and quenched in a water bath. The product was single-phase crystalline $Na_{4.9}GdSi_{3.95}S_{.05}O_{12}$ with an X-ray diffraction pattern similar to those shown in Table I and with hexagonal cell dimensions $a = 22.15$ A, $c = 12.65$ A, and $V = 5376$ A$^3$. The conductivity of a sintered disc prepared by the technique of Example 21 was $7 \times 10^{-2}$ $(\Omega \text{ cm})^{-1}$ at 200° C.

EXAMPLE 23

A mixture of 1.810 g $Na_2CO_3$, 1.346 g $Gd_2O_3$, 1.739 g $SiO_2$ and 0.105 g $Na_2SO_4$ was treated as described in Example 22. The product was single-phase crystalline $Na_{4.8}GdSi_{3.9}S_{.1}O_{12}$ with an X-ray diffraction pattern similar to those shown in Table I and with hexagonal cell dimensions $a = 22.14$ A, $c = 12.66$ A and $V = 5373$ A$^3$. The conductivity of a sintered disc prepared by the technique of Example 21 was $4 \times 10^{-2} (\Omega \text{ cm})^{-1}$ at 200° C.

EXAMPLES 24–26

Each of these three examples was prepared in the following manner. The quantities of $Na_2CO_3$, $Gd_2O_3$, $SiO_2$ and $GeO_2$ shown in Table V were ground in an agate mortar, heated in a Pt crucible to 500° C for 4 hr, and 1000° C for 4 hr. Each product was ball-milled in an agate planetary mill for 2 hr, heated to 900° C for 16 hr and quenched in a water bath. Each product was a single phase crystalline material with an X-ray diffraction pattern similar to those shown in Table I and had the hexagonal cell dimensions shown in Table V. Discs were prepared by the technique of Example 1 and heated at 900° C for 24 hr and the ionic conductivities measured. The ionic conductivities at 200° C are shown in Table V.

furnace cooled. The sintered product was ground in an agate mortar, reheated to 1100° C for 16 hr and quenched in air. The resulting powder $Na_{4.70}Y_{.70}Zr_{.30}Si_4O_{12}$ gave a single phase X-ray diffraction pattern similar to those shown in Table I and corresponding to the rhombohedral cell with the hexagonal parameters $a = 21.99$ A, $c = 12.58$ A, and $V = 5271$ A$^3$. A disc of this material made by cold pressing a portion of the finely ground powder product at 60,000 psi and heating to 1100° C for 16 hr, had a density of 2.69 g/cm$^3$, corresponding to 95% theoretical density. The conductivity at 200° C was $2.0 \times 10^{-2}$ ohm$^{-1}$cm$^{-1}$.

EXAMPLE 30

A mixture of 2.358 g $Na_2CO_3$, 0.748 g $Y_2O_3$, 0.598 g $HfO_2$ and 2.275 g $SiO_2$ was heated in a platinum crucible at 650° C for 16 hr, 900° C for 8 hr, 1100° C for 16 hr and furnace cooled. The sintered product was then ground in an agate mortar and refired at 1100° C for 20 hr and quenched in air. The polycrystalline product $Na_{4.70}Y_{.70}Hf_{.30}Si_4O_{12}$ gave an X-ray diffraction pattern similar to those shown in Table I and corresponding to the rhombohedral cell with the hexagonal parameters $a = 22.00$ A, $c = 12.58$ A, and $V = 5269$ A$^3$. A portion of this finely ground powder was pressed into a disc at 60,000 psi and then heated at 1100° C for 16 hr. The disc was allowed to cool with the furnace to 750° C, then was quenched in air. The conductivity at 200° C was $2.6 \times 10^{-2}$ ohm$^{-1}$cm$^{-1}$.

TABLE V

| Example No. | Product | Reactants | | | | Hexagonal Unit Cell Parameters | | | Ionic Conductivity at 200° C $(\Omega \text{ cm}^{-1})$ |
|---|---|---|---|---|---|---|---|---|---|
| | | $Na_2CO_3$ | $Gd_2O_3$ | $SiO_2$ | $GeO_2$ | a(A) | c(A) | V(A$^3$) | |
| 24 | $Na_5GdSi_3GeO_{12}$ | 1.812g | 1.240g | 1.233g | 0.715g | 22.28 | 12.72 | 5472 | $5.2 \times 10^{-2}$ |
| 25 | $Na_5GdSi_2Ge_2O_{12}$ | 1.708g | 1.168g | 0.775g | 1.348g | 22.45 | 12.82 | 5596 | $1.1 \times 10^{-2}$ |
| 26 | $Na_5GdGe_4O_{12}$ | 1.532g | 1.048g | | 2.419g | 22.78 | 12.99 | 5840 | |

EXAMPLE 27

A mixture of 1.958 g $Na_2CO_3$, 0.644 g $Sm_2O_3$, 0.622 g $Nd_2O_3$ and 1.776 g $SiO_2$ was heated at 500° C for 4 hr, and 1000° C for 4 hr. The product was ground in an agate planetary ball-mill for 2 hr and heated to 900° C for 16 hr and quenched in a water bath. This product was ground again for 2 hr in the agate ball mill and heated at 1000° C for 24 hr and quenched again in a water bath. The product was single phase crystalline $Na_5Sm_{.5}Nd_{.5}Si_4O_{12}$ with an X-ray diffraction pattern similar to those shown in Table I and with hexagonal cell dimensions $a = 22.18$ A, $c = 12.68$ A, and $V = 5404$ A$^3$.

EXAMPLE 28

A mixture of 1.951 g $Na_2CO_3$, 1.027 g $Sm_2O_3$, 0.252 g $Pr_6O_{11}$ and 1.770 g $SiO_2$ was ground in an agate mortar, heated to 500° C for 4 hr and 1000° C for 16 hr. The product was ground in a planetary agate ball mill for 2 hr, then heated to 900° C for 16 hr and quenched in a water bath. The product was single phase crystalline $Na_5Sm_{.8}Pr_{.2}Si_4O_{12}$ with an X-ray diffraction pattern similar to those shown in Table I and hexagonal cell dimensions $a = 22.19$ A, $c = 12.67$ A, and $V = 5404$ A$^3$.

EXAMPLE 29

A mixture of 2.481 g $Na_2CO_3$, 0.787 g $Y_2O_3$, 0.629 g $ZrO_2$ and 2.394 g $SiO_2$ was heated in a platinum crucible at 650° C for 16 hr, 900° C for 6 hr, 1100° C for 16 hr and

EXAMPLE 31

A mixture of 2.551 g $Na_2CO_3$, 1.043 g $Y_2O_3$, 0.277 g $Th(NO_3)_4.5H_2O$ and 2.337 g $SiO_2$ was heated in a platinum crucible to 750° C for 16 hr, 900° C for 8 hr, 1100° C for 18 hr and furnace cooled. The sintered powder was ground in an agate mortar and reheated to 1100° C for 12 hr, furnace cooled to 550° C and quenched in air. The product was still impure and was ball-milled in an agate mill for 1 hr, and reheated to 1100° C for 16 hr. X-ray analysis was performed on the product which still contained one diffraction line due to $ThO_2$ impurity. The product consisted mainly of $Na_{4.95}Y_{.95}Th_{.05}Si_4O_{12}$ which has a diffraction pattern similar to those shown in Table I corresponding to the rhombohedral cell with hexagonal parameters $a = 22.04$ A, $c = 12.60$ A, and $V = 5304$ A$^3$. A portion of the powder was pressed into a disc at 60,000 psi, then was heated to 1100° C for 16 hr, and furnace cooled. The conductivity at 200° C was 3.2 $\times 10^{-2}$ ohm$^{-1}$cm$^{-1}$.

EXAMPLE 32

A mixture of 2.469 g $Na_2CO_3$, 0.658 g $Y_2O_3$, 0.327 g $Nd_2O_3$, 0.239 g $ZrO_2$ and 2.333 g $SiO_2$ was heated in a Pt crucible to 650° C for 5 hr, 1100° C for 28 hr, then quenched in air. The sintered product was ball-milled for 1 hr in an agate mill, then reheated to 900° C for 20 hr and quenched in air. The single phase $Na_{4.8}Y_{.6}Nd_{.2}Zr_{.2}Si_4O_{12}$ product had an X-ray pattern similar to those shown in Table I and corresponding to the rhombohedral cell with the hexagonal parameters $a =$ 22.03 A, $c = 12.58$ A, and $V = 5289$ A$^3$. A portion of the powder was pressed into a disc at 60,000 psi and then heated to 990° C for 16 hr, furnace cooled to 380° C and quenched. The conductivity at 200° C was $4 \times 10^{-2}$ ohm$^{-1}$ cm$^{-1}$.

EXAMPLE 33

A mixture of 2.458 g Na$_2$CO$_3$, 0.534 g Y$_2$O$_3$, 0.637 g Nd$_2$O$_3$, 0.117 g ZrO$_2$ and 2.275 g SiO$_2$ was heated in a Pt crucible to 650° C for 5 hr, 1100° C for 28 hr, then quenched in air. The sintered product was ball-milled for 1 hr in an agate mill, then reheated to 900° C for 20 hr and quenched in air. The single phase Na$_{4.9}$Y$_{.50}$Nd$_{.40}$Zr$_{.10}$Si$_4$O$_{12}$ product had an X-ray pattern similar to those shown in Table I and corresponding to the rhombohedral cell with the hexagonal parameters $a = 22.10$ A, $c = 12.63$ A and $V = 5339$ A$^3$. A portion of the powder was pressed into a disc at 60,000 psi and then heated to 990° C for 16 hr, furnace cooled to 380° C and quenched. The conductivity at 200° C was $4.5 \times 10^{-2}$ ohm$^{-1}$ cm$^{-1}$.

EXAMPLE 34

A mixture of 1.943 g Na$_2$CO$_3$, 1.278 g Gd$_2$O$_3$ and 1.779 g SiO$_2$ corresponding to the nominal composition Na$_5$GdSi$_4$O$_{12}$ + 10% Na$_2$Si$_2$O$_5$ was ground in a mortar, heated in a platinum crucible at 500° C for 4 hr, and 1000° C for 4 hr. The product was ground in an agate ball mill, heated to 800° C for 16 hr, 1000° C for 16 hr and cooled slowly with the furnace. X-ray diffraction of the product showed predominantly Na$_5$GdSi$_4$O$_{12}$ with a small amount of an unidentified phase. The disc prepared by the technique described in Example 1 showed $d = 2.99$ g/cc (95% theoretical density) and a conductivity of $1.2 \times 10^{-1}$ ($\Omega$ cm)$^{-1}$ at 200° C. The conductivity is thus improved over pure Na$_5$GdSi$_4$O$_{12}$ at 200° C.

EXAMPLE 35

A mixture of 1.729 g Na$_2$CO$_3$, 0.28 g BaCO$_3$, 1.286 g Gd$_2$O$_3$, and 1.705 g SiO$_2$ was ground in an agate mortar and heated in a Pt crucible at 500° C for 4 hr, and 1000° C for 4 hr. The product was ball-milled in an agate planetary mill for 2 hr, heated at 900° C for 16 hr and quenched in a water bath. X-ray analysis indicated that the product was primarily of the rhombohedral structure of the type indicated in Table I. A small amount (5–15% approximately) was a phase believed to be Na$_3$BaGdSi$_4$O$_{12}$.

Using the technique described in Example 1 a disc was prepared from the above product in order to measure the conductivity as described in Example 1. The conductivity at 200° C was $7 \times 10^{-2}$ ($\Omega$ cm)$^{-1}$. This shows that small amounts of this impurity phase do not reduce conductivity significantly but result in a readily sinterable product.

EXAMPLE 36

A mixture of 1.447 g Na$_2$CO$_3$, 0.674 g BaCO$_3$, 1.238 g Gd$_2$O$_3$ and 1.641 g SiO$_2$ was ground in an agate mortar and heated in a Pt crucible at 500° C for 4 hr, and 1000° C for 4 hr. The product was ground in an agate ball mill for 2 hr, heated at 1000° C for 16 hr and quenched in a water bath. The X-ray diffraction pattern of the product showed 1) a phase having the rhombohedral structure shown in Table I with the cell dimensions of Na$_5$GdSi$_4$O$_{12}$ ($a = 22.13$ A and $c = 12.66$ A) and 2) an impurity phase thought to be Na$_3$BaGdSi$_4$O$_{12}$. A disc prepared by the technique described in Example 1 showed an ionic conductivity of $3 \times 10^{-2}$ ($\Omega$ cm)$^{-1}$ at 200° C. The fact that such a large amount of impurity phase does not strongly reduce the ionic conductivity suggest that this impurity is also a good ionic conductor. Subsequent measurements have verified this.

EXAMPLE 37

A mixture of 1.915 g Na$_2$CO$_3$, 0.310 g BaCO$_3$, 0.887 g Y$_2$O$_3$ and 1.888 g SiO$_2$ was ground in a mortar, heated in a platinum crucible at 500° C for 4 hr, and 1000° C for 4 hr. The product was ground in a ball mill for 2 hr, heated at 800° C for 16 hr, 1000° C for 16 hr and quenched in a water bath. The product was composed of two phases— 1) a rhombohedral phase with cell dimensions corresponding to Na$_5$YSi$_4$O$_{12}$ and 2) an impurity phase thought to be Na$_3$BaYSi$_4$O$_{12}$. A disc prepared according to the technique described in Example 1 showed an ionic conductivity of $2.5 \times 10^{-2}$ ($\Omega$ cm)$^{-1}$ at 200° C. As in Example 36, the fact that a large amount of impurity phase does not lower the conductivity significantly suggests that the impurity phase is a good ionic conductor. Subsequent measurements have verified this.

EXAMPLE 38

A mixture of 1.530 g Na$_2$CO$_3$, 1.056 g Tb$_2$O$_3$ and 2.415 g GeO$_2$ was ground in a mortar, placed in a platinum crucible, heated to 500° C for 4 hr and 900° C for 4 hr. The product was ground in an agate ball mill, reheated to 900° C for 16 hr and quenched in a water bath. The single phase crystalline Na$_5$TbGe$_4$O$_{12}$ gave an X-ray diffraction pattern similar to those shown in Table I. Hexagonal cell dimensions are $a = 22.74$ A, $c = 12.97$ A and $V = 5808$ A$^3$. A disc prepared by the technique described in Example 1 had an ionic conductivity of $1.6 \times 10^{-3}$ ($\Omega$ cm)$^{-1}$ at 200° C.

EXAMPLES 39–45

Examples 39–45 were all prepared according to the procedure outlined in Example 38 using the mixture of starting materials shown in Table VI. The powder products all gave single phase X-ray patterns characteristic of the rhombohedral structure and similar to those shown in Table I with hexagonal cell dimensions shown in Table VI. Discs of several of these samples were prepared as described in Example 1. These conductivities are listed in Table VI. Discs prepared from the compositions Na$_5$YbGe$_4$O$_{12}$ and Na$_5$ErGe$_4$O$_{12}$ reacted with liquid Na metal.

TABLE VI

| Example No. | Product | Reactants | | | Hexagonal Unit Cell Parameters | | | Ionic Conductivity at 200° C ($\Omega$ cm)$^{-1}$ |
| --- | --- | --- | --- | --- | --- | --- | --- | --- |
| | | Na$_2$CO$_3$ | GeO$_2$ | Other | a(A) | c(A) | V(A$^3$) | |
| 38 | Na$_5$TnGe$_4$O$_{12}$ | 1.530g | 2.415g | 1.056g Tb$_2$O$_3$ | 22.74 | 12.97 | 5808 | $1.6 \times 10^{-3}$ |
| 39 | Na$_5$YGe$_4$O$_{12}$ | 1.664g | 2.627g | 0.709g Y$_2$O$_3$ | 22.62 | 12.95 | 5735 | |
| 40 | Na$_5$LuGe$_4$O$_{12}$ | 1.502g | 2.371g | 1.128g Lu$_2$O$_3$ | 22.58 | 12.90 | 5697 | |
| 41 | Na$_5$YbGe$_4$O$_{12}$ | 1.505g | 2.376g | 1.119g Yb$_2$O$_3$ | 22.61 | 12.92 | 5718 | Reacted with Na |
| 42 | Na$_5$TmGe$_4$O$_{12}$ | 1.512g | 2.387g | 1.101g Tm$_2$O$_3$ | 22.63 | 12.92 | 5734 | $7.6 \times 10^{-3}$ |
| 43 | Na$_5$ErGe$_4$O$_{12}$ | 1.515g | 2.392g | 1.094g Er$_2$O$_3$ | 22.67 | 12.95 | 5763 | Reacted with Na |
| 44 | Na$_5$HoGe$_4$O$_{12}$ | 1.519g | 2.398g | 1.083g Ho$_2$O$_3$ | 22.68 | 12.96 | 5773 | $6.9 \times 10^{-3}$ |

TABLE VI-continued

| Example No. | Product | Reactants | | | Hexagonal Unit Cell Parameters | | | Ionic Conductivity at 200° C $(\Omega\ cm)^{-1}$ |
|---|---|---|---|---|---|---|---|---|
| | | $Na_2CO_3$ | $GeO_2$ | Other | a(A) | c(A) | V(A$^3$) | |
| 45 | $Na_5DyGe_4O_{12}$ | 1.523g | 2.405g | 1.072g $Dy_2O_3$ | 22.72 | 12.97 | 5795 | $2.8 \times 10^{-3}$ |

EXAMPLE 46

Electrowinning of Sodium from NaCl-AlCl$_3$ Melts

An electrowinning cell as shown in FIG. 3 was constructed. A solid electrolyte disc 16 with the composition $Na_{4.9}Gd_{.9}Zr_{.1}Si_4O_{12}$ was sealed to the end of a glass tube 20 using Cotronics (New York, N.Y.) 940 ceramic cement 30. This constituted the anode compartment which contained molten NaAlCl4 electrolyte 40. A glassy carbon rod 50 submerged in the molten electrolyte served as the anode. Nickel felt 60 (Brunswick Corp. Technical Products Div., Skokie, Ill.: Type FM1205) was pressed against the solid electrolyte and served as the initial cathode. During electrolysis when sodium was produced at the solid electrolyte-nickel interface, sodium itself served as the cathode. The cell was operated in an argon dry box 70 at a temperature of 200° C. Chlorine generated at the anode was removed through opening 80 in tube 20 and trapped outside of the dry box.

The effective area of the solid electrolyte was 0.5 cm$^2$. When 5-6 volts d.c. were applied using a PAR Potentiostat (Model 173), 10-20 milliamps of current were passed through the cell. The number of coulombs was determined using a Princeton Applied Research (Princeton, N.J.) Coulometer (Model 179). A total of 801 coulombs was passed and the cell was disconnected. The sodium which had accumulated at the cathode was dissolved in 50 ml of methanol. The resulting solution was titrated with 0.1 N HCl solution and the amount of sodium calculated. It was found that 5.5 milliequivalents of sodium were produced during the electrolysis. At 100% current efficiency, 8.3 milli equivalents would have been produced. Therefore, the above cell operated at 66% current efficiency.

EXAMPLE 47

Electrowinning of Sodium from Sodium Amalgam

An electrowinning cell similar to that shown in FIG. 3 was constructed. A sodium amalgam was prepared by dissolving 0.46 g Na metal in 100.3 g of mercury. This was placed into a glass beaker with a nickel wire serving as the anode terminal.

The cathode compartment consisted of an 18 mm i.d. glass tube to which was sealed a disc of $Na_5GdSi_4O_{12}$ 2.210 cm diameter and 0.183 cm thick. Nickel felt was placed inside the glass tube in contact with the solid electrolyte and served as the initial cathode contact. This cathode compartment was lowered into the amalgam compartment. The cell was heated in an argon atmosphere to 170° C and connected to a PAR Potentiostat which served as the power supply. The electrolysis was performed at 2 volts and the current density varied from 50 to 15 ma/cm$^2$. After 85.5% of the sodium was removed from the amalgam (based on the amount of charge passed through the cell), the deposited sodium at the cathode was dissolved in methanol, diluted with water and titrated with a standard solution of HCl. These results indicated that sodium had been removed from the amalgam with 99% current efficiency.

EXAMPLE 48

Na-Na$_2$S$_5$ Battery

A sodium-sulfur cell shown in FIG. 4 was assembled in an argon atmosphere from the following components: an anode 6 consisting of 0.46 g Na metal, a solid electrolyte 7 with the composition $Na_{4.9}Gd_{.9}Zr_{.1}Si_4O_{12}$, 1.10 cm diameter, 0.38 cm thick, a catholyte 8 consisting of 2.24 g $Na_2S_4$, and a cathode 9 consisting of a vitreous carbon rod (3 × 150 mm) wrapped in graphite felt.

Figure 5:
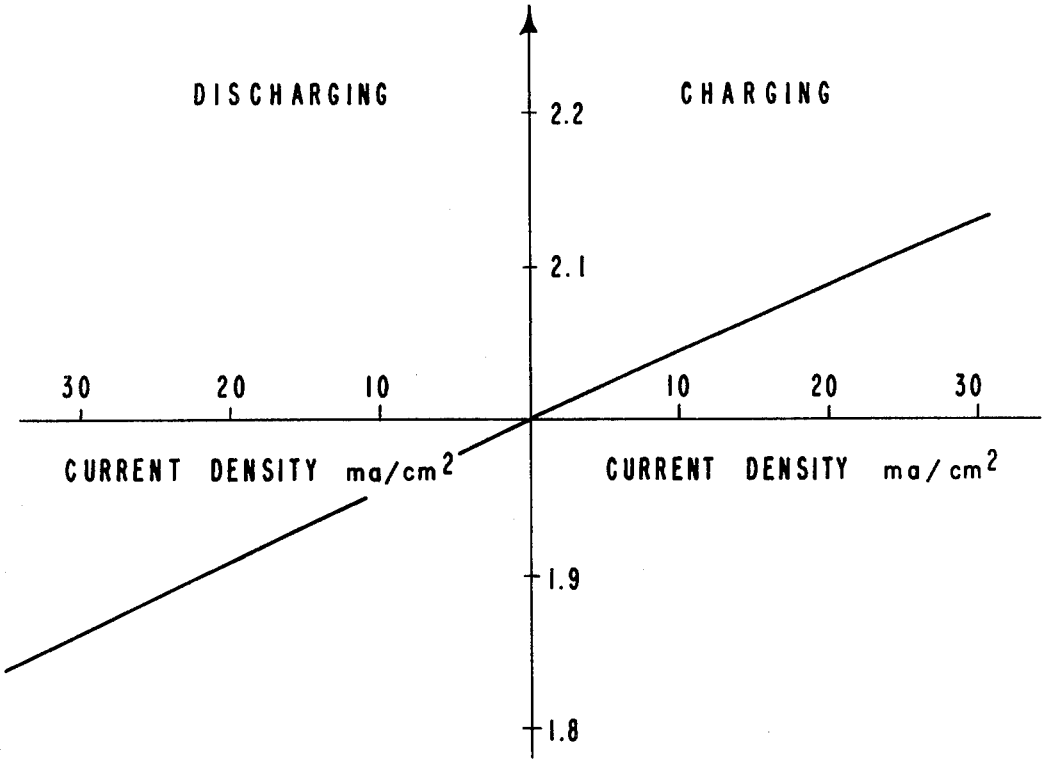
FIG. 5 is a graph of the cell characteristics of the cell illustrated in FIG. 6 during charging and discharging.

The solid electrolyte was sealed to a Pyrex glass tube 10 using Cotronics 940 ceramic cement 11 in a manner similar to Example 46. The effective area of the electrolyte was 0.5 cm$^2$. Sodium sulfide ($Na_2S_4$) was placed inside the tube and the vitreous carbon rod 9 connected to a platinum wire 12 served as a cathode terminal. The anode compartment consisted of a 10 ml beaker 13 containing the sodium. A nickel wire 14 served as the anode terminal. The cathode compartment was placed inside the anode compartment in such a way that the solid electrolyte 7 contacted metallic sodium 6. The cell was placed inside an oven 15 in the argon atmosphere drybox. The cell was heated to 325° C where the sodium and sodium tetrasulfide were molten. the cell characteristics were determined with a PAR Potentiostat (Model 173) during discharge and charge, and the results are shown in FIG. 5. The open circuit voltage of the battery was 2.0 volts.

EXAMPLE 49

Na-TiS$_2$ Battery

A cell shown in FIG. 6 was assembled in an argon atmosphere from the following components: an anode 21 was fabricated from Ni sponge and 0.11 g of Na foil, a solid electrolyte disc 22 of composition $Na_5GdSi_4O_{12}$ 2.5 cm in diameter and 0.260 cm thick and a solid TiS$_2$ cathode 23.

Titanium disulfide used as the cathode was prepared in the following manner. 2.138 g Ti metal and 2.862 g sulfur were placed in a silica tube which was evacuated to 10$^{-6}$ mm Hg, sealed, and placed in a furnace. It was heated very gradually to 1000° C, held at this temperature for 16 hours, and allowed to cool with the furnace. The resulting product was gold in color and gave an X-ray pattern of pure TiS$_2$.

The anode and cathode were pressed against opposite faces of the solid electrolyte disc by means of springs 24. This pressure was transmitted to the anode and cathode by stainless steel 25 faced brass slugs 26. The brass slugs 26 were sealed to Pyrex glass cell wall 31, 32 by rubber O-rings 29. The springs were electrically insulated from the brass slugs by glass insulators 27. External electrical connections 28 were connected to the brass slugs. The area of the Na in contact with the solid electrolyte was 1.27 cm$^2$. The cell was encased in glass sleeves 31 and 32, one side of which used a rubber O-ring 33 to seal the cell. The clamped cell in the argon atmpsphere dry-box was placed inside an oven.

In a first attempt, a cold pressed disc of $TiS_2$ (0.665 gm) was pressed against the surface of the solid electrolyte, and the battery tested at 125° C. A cell resistance $>10^5$ ohm was observed and about $10^{-2}$ coulomb was drawn from the cell. The cell was then disassembled in the dry box.

In the dry box, some $TiS_2$ flaky powder was burnished into the $Na_5GdSi_4O_{12}$ surface which abuts the $TiS_2$ cathode by using a stainless steel spatula. This burnished film had a smooth, metallic greenish luster. Additional $TiS_2$ powder was placed between this film and the disc of $TiS_2$. The cell was reassembled and heated to $\sim 110°$ C. At this operating temperature the cell provided an open circuit output voltage of 2.1 volt (Na electrode was negative) and 1.8 volts when a current density of $10^{-4}$ amps/cm$^2$ was being drawn. The output voltage was measured with a Princeton Applied Research Model 173 Potentiostat/Galvanostat and the charge was measured with a Princeton Applied Research Model 179 Coulometer. This cell resistance was about $2.5 \times 10^3$ ohms, considerably lower than that of the first attempt to use this cell. The volume of Na transported through the $Na_5GdSi_4O_{12}$ electrolyte estimated from the charge flow ($\sim 1$ coulomb) during the discharge cycle is about $0.23 \times 10^{-3}$ cm$^3$. This is a layer of Na 1.27 cm$^2 \times \sim 2$ microns thick. It was suspected that only the burnished-on layer of $TiS_2$ was accumulating the Na that moved through the $Na_5GdSi_4O_{12}$ and that an improved interface between the bulk $TiS_2$ and the $Na_5GdSi_4O_{12}$ would significantly increase the battery capacity and decrease the cell resistance.

Figure 7:
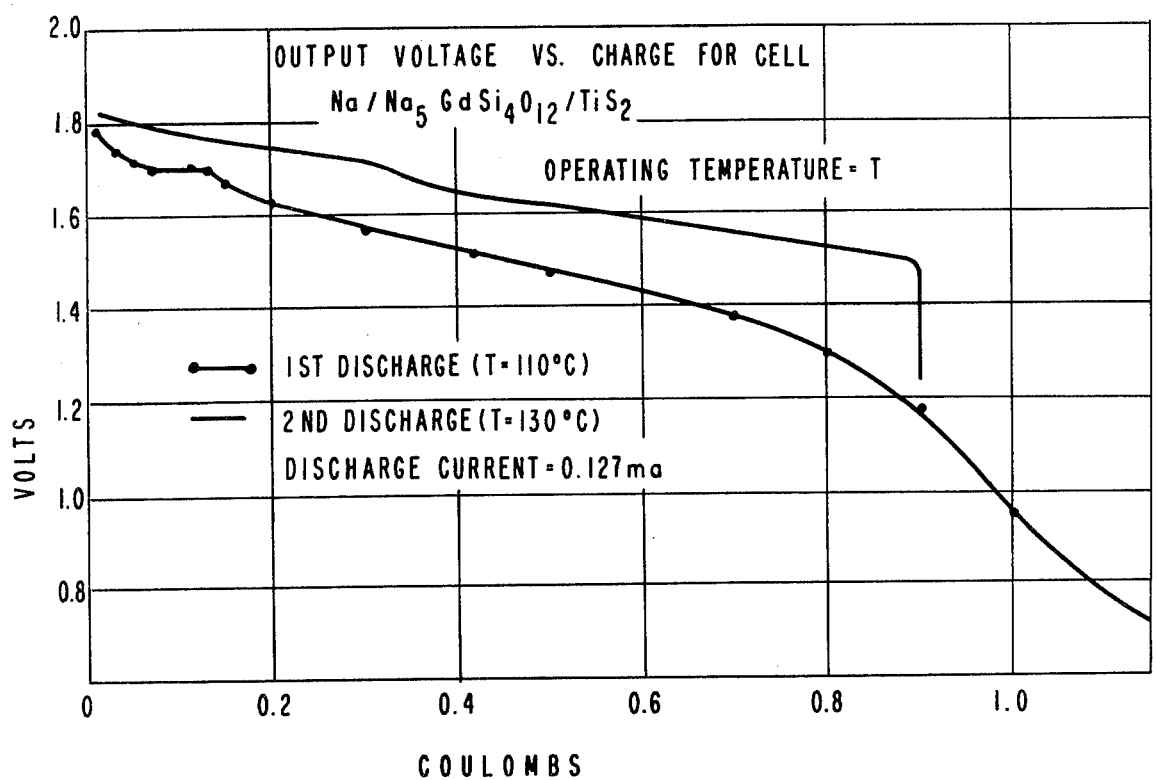
FIG. 7 is a graph showing voltage vs. charge flow for the cell illustrated in FIG. 6.

In attempting to recharge the cell after the first discharge cycle, only about 0.06 coulomb could be replaced before the cell impedance increased dramatically. It was suspected that the $TiS_2$ cathode contact was not conducting the Na to the surface of the disc and that only the Na at the interface was being depleted, accounting for the rapid increase in cell impedance upon charging. A second discharge cycle during which again approximately 1 coulomb of charge flowed was observed at 130° C. Plots of the voltage versus charge flow for the two cycles are shown in FIG. 7.

What is claimed is:

1. The method of conducting sodium ions utilizing a composition having (a) the formula $Na_{5-x}\square_xGd_{1-y-x}M_yM'_xSi_{4-z}Ge_zO_{12}$ wherein M is yttrium or at least one of the rare earths other than Gd, M' is $Zr^{4+}$, $Hf^{4+}$, or $Th^{4+}$, $\square$ is a sodium vacancy to preserve charge neutrality, x is 0 to about 0.5 when $Zr^{4+}$ or $Hf^{4+}$ is included in M' and 0 to about 0.1 when $Th^{4+}$ is included in M', y is 0 to 1, and z is 0 to 4, with the proviso that $y+x$ is no more than 1, and (b) the crystal structure of the rhombohedral $Na_5YSi_4O_{12}$-type with the space group symmetry R3c.

2. The method of claim 1 utilizing a composition having the formula $Na_{5-x}\square_x Gd_{1-y-x}M_yM'_xSi_4O_{12}$.

3. The method of claim 2 wherein M' is $Zr^{4+}$.

4. The method of claim 2 wherein M is at least one of $Ho^{3+}$, $Sm^{3+}$, $Tb^{3+}$, $Dy^{3+}$, $Nd^{3+}$, $Pr^{3+}$ and $La^{3+}$ and y is
   (1) 0 to 1 when M is $Ho^{3+}$, $Sm^{3+}$, $Tb^{3+}$ or $Dy^{3+}$,
   (2) 0 to about 0.6 when M is $Nd^{3+}$,
   (3) 0 to about 0.4 when M is $Pr^{3+}$, and
   (4) 0 to about 0.2 when M is $La^{3+}$.

5. The method of claim 4 wherein M' is $Zr^{4+}$.

6. The method of claim 2 wherein said composition has the formula $Na_5GdSi_4O_{12}$.

7. The method of claim 2 wherein said composition has the formula $Na_5SmSi_4O_{12}$.

8. The method of claim 2 wherein said composition has the formula $Na_5HoSi_4O_{12}$.

9. The method of claim 2 wherein said composition has the formula $Na_5TbSi_4O_{12}$.

10. The method of claim 2 wherein said composition has the formula $Na_{4.9-4.8}Gd_{.9-.8}Zr_{.1-.2}Si_4O_{12}$.

11. The method of claim 2 wherein said composition has the formula $Na_5Gd_{.8-.4}Nd_{.2-.6}Si_4O_{12}$.

12. The method of claim 2 wherein said composition has the formula $Na_5Gd_{.8}La_{.2}Si_4O_{12}$.

13. The method of claim 2 wherein said composition has the formula $Na_{4.9}Gd_{.7}Nd_{.2}Zr_{.1}Si_4O_{12}$.

14. The method of claim 2 wherein said composition has the formula $Na_5Gd_{.8-.6}Pr_{.2-.4}Si_4O_{12}$.

15. A composition of matter having (a) the formula $Na_{5-x}\square_xGd_{1-y-x}M_yM'_xSi_{4-z}Ge_zO_{12}$ wherein M is at least one of $Ho^{3+}$, $Sm^{3+}$, $Tb^{3+}$, $Dy^{3+}$, $Nd^{3+}$, $Pr^{3+}$ and $La^{3+}$, M' is $Zr^{4+}$, $Hf^{4+}$, or $Th^{4+}$, $\square$ is a sodium vacancy to preserve charge neutrality, z is 0 to 4, x is 0 to about 0.5 when $Zr^{4+}$ or $Hf^{4+}$ is included in M' and 0 to about 0.1 when $Th^{4+}$ is included in M', y is (1) 0 to 1 when M is $Ho^{3+}$, $Sm^{3+}$, $Tb^{3+}$, or $Dy^{3+}$,
   (2) 0 to about 0.6 when M is $Nd^{3+}$,
   (3) 0 to about 0.4 when M is $Pr^{3+}$, and
   (4) 0 to about 0.2 when M is $La^{3+}$, with the proviso that $y + x$ can be no more than 1 and (b) the crystal structure of the rhombohedral $Na_5YSi_4O_{12}$-type with space group symmetry R3c.

16. The composition of claim 15 wherein z is 0.

17. The composition of claim 16 wherein M' is $Zr^{4+}$.

18. The composition of claim 16 wherein x is 0.

19. The composition of claim 17 wherein y is 0.

20. The method of claim 1 wherein the said composition is admixed with up to 20 mole percent $Na_2Si_2O_5$.

21. The method of claim 2 wherein the said composition is admixed with up to 20 mole percent $Na_2Si_2O_5$.

22. The method of claim 4 wherein the said composition is admixed with up to 20 mole percent $Na_2Si_2O_5$.

23. The method of claim 1 wherein the said composition is admixed with about 5-30 mole percent $Na_3BaGdSi_4O_{12}$ or $Na_3BaYSi_4O_{12}$.

24. The method of claim 2 wherein the said composition is admixed with about 5-30 mole percent $Na_3BaGdSi_4O_{12}$ or $Na_3BaYSi_4O_{12}$.

25. The method of claim 4 wherein the said composition is admixed with about 5-30 mole percent $Na_3BaGdSi_4O_{12}$ or $Na_3BaYSi_4O_{12}$.

26. The method of claim 1 wherein the said composition is admixed with about 1-2 mole percent of $Na_2SO_4$ or $Na_3PO_4$.

27. The method of claim 2 wherein the said composition is admixed with about 1-2 mole percent of $Na_2SO_4$ or $Na_3PO_4$.

28. The method of claim 4 wherein the said composition is admixed with about 1-2 mole percent of $Na_2SO_4$ or $Na_3PO_4$.

29. In an electrochemical device having (a) two electrodes, one of which is a sodium-containing electrode capable of supplying sodium ions, (b) a solid electrolyte separating the two electrodes and (c) an inert connecting electrical connector to complete an electrical circuit between the two electrodes, the improvement wherein the solid electrolyte consists essentially of the sodium ion conducting composition of claim 1.

30. The electrochemical device of claim 29 wherein the solid electrolyte is the sodium ion conducting composition $Na_{5-x}\square_x Gd_{1-y-x}M_y M'_x Si_4 O_{12}$.

31. The electrochemical device of claim 29 wherein the solid electrolyte is the sodium ion conducting composition $Na_{5-x}\square_x Gd_{1-y-x}M_y M'_x Si_4 O_{12}$ wherein M is at least one of $Ho^{3+}$, $Sm^{3+}$, $Tb^{3+}$, $Dy^{3+}$, $Nd^{3+}$, $Pr^{3+}$, and $La^{3+}$ and $y$ is
  (1) 0 to 1 when M is $Ho^{3+}$, $Sm^{3+}$, $Tb^{3+}$, or $Dy^{3+}$,
  (2) 0 to about 0.6 when M is $Nd^{3+}$,
  (3) 0 to about 0.4 when M is $Nd^{3+}$, and
  (4) 0 to about 0.2 when M is $La^{3+}$.

32. The electrochemical device of claim 29 wherein the solid electrolyte is the sodium ion conducting composition $Na_5 GdSi_4 O_{12}$.

33. The electrochemical device of claim 29 wherein the solid electrolyte is the sodium ion conducting composition $Na_{4.9-4.8}Gd_{.9-.8}Zr_{.1-.2}Si_4 O_{12}$.

34. The electrochemical device of claim 29 wherein the solid electrolyte composition contains up to 20 mole percent $Na_2 Si_2 O_5$.

35. The electrochemical device of claim 29 wherein the solid electrolyte contains about 5–30 mole percent $Na_3 BaGdSi_4 O_{12}$ or $Na_3 BaYSi_4 O_{12}$.

36. The electrochemical device of claim 29 wherein the solid electrolyte contains about 1–2 mole percent of $Na_2 SO_4$ or $Na_3 PO_4$.

37. The electrochemical device of claim 29 wherein it is an electrolytic cell.

38. The electrochemical device of claim 29 wherein it is a galvanic cell.

39. The galvanic cell of claim 38 wherein the anode is sodium and the cathode is sulfur.

40. The galvanic cell of claim 38 wherein the anode is sodium and the cathode is $TiS_2$.

41. The electrolytic cell of claim 37 which is a $NaCl$-$AlCl_3$-$Na$ electrowinning cell.

42. The electrolytic cell of claim 37 which is a sodium amalgam-sodium electrowinning cell.

* * * * *